(12) United States Patent
Wassmann et al.

(10) Patent No.: US 10,829,456 B2
(45) Date of Patent: Nov. 10, 2020

(54) HALOGEN SUBSTITUTED DIKETONES, PYRAZOLE COMPOUNDS AND PROCESSES FOR THE MANUFACTURE OF PYRAZOLE COMPOUNDS

(71) Applicant: SOLVAY SA, Brussels (BE)

(72) Inventors: Suzanne Wassmann, Hannover (DE); Janis Jaunzems, Hannover (DE); Stefan Mross, Sainte Foy lès Lyon (FR); Jean Fabre, Wettbergen (DE)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 16/071,677

(22) PCT Filed: Jan. 27, 2017

(86) PCT No.: PCT/EP2017/051797
§ 371 (c)(1),
(2) Date: Jul. 20, 2018

(87) PCT Pub. No.: WO2017/129759
PCT Pub. Date: Aug. 3, 2017

(65) Prior Publication Data
US 2019/0031616 A1    Jan. 31, 2019

(30) Foreign Application Priority Data

Jan. 28, 2016 (EP) .................................... 16153112
Mar. 25, 2016 (EP) .................................... 16162487
Oct. 28, 2016 (EP) .................................... 16196175

(51) Int. Cl.
| | | |
|---|---|---|
| C07D 231/18 | (2006.01) | |
| C07C 225/14 | (2006.01) | |
| C07D 231/12 | (2006.01) | |

(52) U.S. Cl.
CPC .......... *C07D 231/18* (2013.01); *C07C 225/14* (2013.01); *C07D 231/12* (2013.01)

(58) Field of Classification Search
None
See application file for complete search history.

(56) References Cited

U.S. PATENT DOCUMENTS

| | | |
|---|---|---|
| 5,545,298 A | 8/1996 | Braun |
| 5,569,782 A | 10/1996 | Braun |
| 5,905,169 A | 5/1999 | Jacobson |
| 2005/0020564 A1 | 1/2005 | Atkinson |
| 2006/0084813 A1 | 4/2006 | Hausmann et al. |
| 2006/0116414 A1 | 6/2006 | Dunkel et al. |
| 2008/0153707 A1 | 6/2008 | Gewehr et al. |
| 2010/0184994 A1 | 7/2010 | Nett et al. |
| 2011/0040096 A1 | 2/2011 | Zierke et al. |
| 2011/0301181 A1 | 12/2011 | Maue |

FOREIGN PATENT DOCUMENTS

| | | |
|---|---|---|
| EP | 0569912 A1 | 11/1993 |
| EP | 0694523 A1 | 1/1996 |
| EP | 1644306 B1 | 8/2011 |
| EP | 2297111 B1 | 6/2012 |
| JP | 2006273844 A | 10/2006 |
| WO | 0117939 A1 | 3/2001 |
| WO | 03070705 A1 | 8/2003 |
| WO | 04035589 A1 | 4/2004 |
| WO | 06015866 A1 | 2/2006 |
| WO | 06087343 A1 | 8/2006 |
| WO | 07009717 A1 | 1/2007 |
| WO | 07031323 A1 | 3/2007 |
| WO | 07048556 A1 | 5/2007 |
| WO | 08152138 A2 | 12/2008 |
| WO | 09021987 A1 | 2/2009 |
| WO | 10000871 A2 | 1/2010 |
| WO | 10012442 A2 | 2/2010 |
| WO | 12010692 A1 | 1/2012 |
| WO | 12055864 A1 | 5/2012 |
| WO | 14195929 A2 | 12/2014 |
| WO | 15097658 A1 | 7/2015 |

OTHER PUBLICATIONS

Rosa, Fernanda A. et al., "N- and C-acylation in .beta.-enamino ketones: structural effects on regiocontrol", Synlett, No. 20, Sep. 4, 2007 (Sep. 4, 2007), pp. 3165-3171.

Mustapha Soufyane et al., "Synthesis of some fluorinated nitrogen heterocycles from (diethylaminomethylene) hexafluoroacetylacetone", Tetrahedron Letters, vol. 48, Jan. 10, 1993 (Jan. 10, 1993), pp. 7737-7740.

Gordon B. Blackwell et al., "Polyhalogeno-allenes and acetylenes. Part 15. Dipolar cycloadditions of N-phenlsydnone and aryl azides to perfluoropropadiene and perfluoropropyne", Journal of the Chemical Society, Perkin Transactions 1: Organic and Biorganic Chemistry, vol. 7, Jan. 10, 1982 (Jan. 10, 1982), pp. 2207-2210.

Ota Norio et al., "A convenient synthesis of fluorine-containing dihydrobenzo(b)(1,4) diazepinols and its application to a synthesis of novel n-sulfinylanilines", Heterocycles, Japan Institute of Heterocyclic Chemistry, vol. 76, No. 2, Jan. 1, 2008 (Jan. 1, 2008), pp. 1205-1217.

Etsuji Okada et al., "Facile synthetic methods for 3- and 5-trifluoromethyl-4-trifluoroacetyl-pyrazoles and their conversion into pyrazole-4-carboxylic Acids", Heterocycles : An International Journal for Reviews and Communications in Heterocyclic Chemistry, Japan Institute of Heterocyclic Chemistry, JP, vol. 34, No. 4, Jan. 1, 1992 (Jan. 1, 1992), pp. 791-798.

B. V. Ioffe et al., "Synthesis and Properties of Monoalkylhydrazones", Translated from Zhurnal Organicheskoi Khimii, vol. 4, No. 6, Jun. 1968, pp. 986-992.

(Continued)

*Primary Examiner* — Kamal A Saeed

(57) ABSTRACT

The present invention concerns new halogen substituted diketone compounds, new pyrazole compounds, processes for the manufacture of pyrazole compounds and processes for the manufacture of agrochemical or pharmaceutical compounds.

18 Claims, No Drawings

(56) References Cited

OTHER PUBLICATIONS

Tietze L.F. et al., "Synthesis of Alkyl Propanoates by a Haloform Reaction of a Trichloro Ketone: Ethyl 3,3-Diethoxypropanoate", Organic Syntheses, vol. 69, 1990 pp. 238-244.
E. Schmitt et al., "In Situ Generated Fluorinated Iminium Salts for Difluoromethylation and Difluoroacetylation", Org. Lett., vol. 17, No. 18, 2015, pp. 4510-4513.

HALOGEN SUBSTITUTED DIKETONES, PYRAZOLE COMPOUNDS AND PROCESSES FOR THE MANUFACTURE OF PYRAZOLE COMPOUNDS

This application is a U.S. national stage entry under 35 U.S.C. § 371 of International Application No. PCT/EP2017/051797 filed Jan. 27, 2017, which claims priority to European application No. 16153112.4 filed Jan. 28, 2016, European application No. 16162487.9 filed Mar. 25, 2016, and European application No. 16196175.0 filed on Oct. 28, 2016. The entire contents of these applications are explicitly incorporated herein by this reference.

The present invention concerns new halogen substituted diketone compounds, new pyrazole compounds, processes for the manufacture of pyrazole compounds and processes for the manufacture of agrochemical or pharmaceutical compounds.

3-halomethylpyrazole-4-yl carboxylic acids and esters are valuable intermediates in the synthesis of agrochemical and pharmaceutical active ingredients. Agrochemical active ingredients which contain such pyrazole building blocks are, for example, 2'-[1,1'-bicycloprop-2-yl]-3-(difluoromethyl)-1-methylpyrazole-4-carboxanilide (Sedaxane), as described, for example, in WO2006015866, 3-(difluoromethyl)-1-methyl-N-[2-(3',4',5'-trifluorophenyl)phenyl]pyrazole-4-carboxamide (Fluxapyroxad), as described, for example, in WO2006087343, N-(3',4'-Dichloro-5-fluorobiphenyl-2-yl)-3-(difluoromethyl)-1-methylpyrazole-4-carboxamide (Bixafen), as described, for example, in WO2003070705, 3-(Difluoromethyl)-1-methyl-N-[1,2,3,4-tetrahydro-9-(1-methylethyl)-1,4-methanonaphthalen-5-yl]-1H-pyrazole-4-carboxamide (Isopyrazam), as described, for example, in WO2004035589, (RS)—N-[9-(Dichloromethylen)-1,2,3,4-tetrahydro-1,4-methanonaphthalin-5-yl]-3-(difluoromethyl)-1-methyl-1H-pyrazole-4-carboxamide (Benzovindiflupyr), as described, for example, in WO07048556. Generally, 3-halomethylpyrazole-4-yl carboxylic acids, often obtained by hydrolysis of their esters, are converted into the carboxamides, for example after conversion into the 3-halomethylpyrazole-4-yl carboxylic acid halide. Other conversions, wherein the carboxamide is generated directly from the ester or acid, have also been described, such as in WO2012055864 and WO 2007/031323. All foregoing cited patent applications are hereby incorporated for all purposes.

EP2297111 B1 describes the manufacture of 3-halomethylpyrazole-4-yl carboxylic esters starting from 2-(aminomethylidene)-3-oxobutyric esters.

The invention concerns thus a compound according to formula (I)

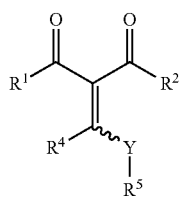

(I)

The residues $R^1$, $R^2$, $R^4$, $R^5$ and Y will be defined in the subsequent description.

The invention relates further to a process for manufacturing a compound according to formula (II)

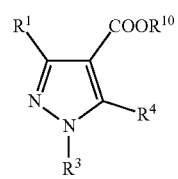

(II)

which comprises the step of reacting a compound of formula (I) with a compound of formula (III), (VIII) or (V)

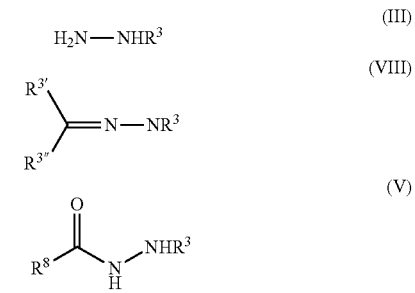

wherein $R^3$ and $R^{10}$ will be described in detail in the subsequent description, and $R^1$ and $R^4$ are the same as described for the compounds of formula (I) in the subsequent description.

The invention further concerns a compound of formula (VII)

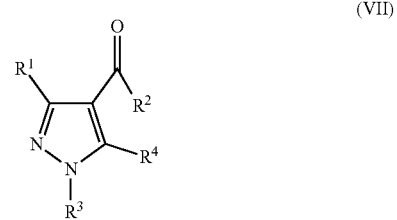

(VII)

wherein $R^1$, $R^2$, $R^3$ and $R^4$ are defined in the subsequent description, and a process for manufacturing the same.

In another aspect, the invention concerns the process for the manufacture of an agrochemical or pharmaceutical compound, which comprises the process for the manufacture of the compounds of formula (II) or (VII), or both processes, mentioned above. In particular, when $R^{10}$ is H in (II), often the carboxylic function is activated by formation of the carboxylic acid halide or anhydride, and subsequent reaction with an amine of formula (VI) NHR$^{12}$Q, wherein $R^{12}$ is selected from the group consisting of H, $C_1$-$C_{12}$-alkyl, $C_2$-$C_6$ alkenyl or $C_3$-$C_8$-cycloalkyl group, wherein H and $C_1$-$C_4$-alkyl are preferred, wherein Q is an optionally substituted aryl or heteroaryl group. In another process for the manufacture of an agrochemical or pharmaceutical compound, which comprises the process for the manufacture of the compounds of formula (II), when $R^{10}$ is selected from the group consisting of $C_1$-$C_{12}$-alkyl, $C_2$-$C_6$ alkenyl or $C_3$-$C_8$-cycloalkyl group, especially when $R^{10}$ is $C_1$-$C_4$-alkyl, is described in WO2012055864, wherein the compound of formula (II) is contacted with an amine of formula (VI) NR$^{12}$HQ, wherein $R^{12}$ is defined as above, wherein Q is an optionally substituted aryl or heteroaryl group, in the presence of at least one base. In yet another process for the manufacture of an agrochemical or pharmaceutical compound, the process comprises a step of reacting (VII) with an amine of formula (VI) $NR^{12}HQ$, optionally after a step of converting (VII) into (II) and optionally activation of (II) when $R^{10}$ is H, for example by conversion into the halide or anhydride. Such a process can also comprise a step of manufacturing a compound of formula (VII) from (I). In one particular embodiment, (VII) is used for the manufacture of an agrochemical or pharmaceutical compound without intermediate conversion onto the corresponding carboxylic acid and/or carboxylic acid halide or anhydride, by reaction with (VI), optionally in the presence of at least one base which is not (VI). The at least one base which is not (VI) preferably is a dialkylamine or trialkylamine, for example triethylamine.

In the present invention, designations in singular are intended to include the plural; for example, "a solvent" is intended to denote also "more than one solvent" or "a plurality of solvents".

In the context of the present invention, the term "comprising" is intended to include the meaning of "consisting of".

When a double bond is depicted in a particular E/Z geometry, this is intended to also denote the other geometric form as well as mixtures thereof. A wavy bond is intended to denote the E geometry, the Z geometry and any mixture thereof.

The first compounds of the invention have the formula (I)

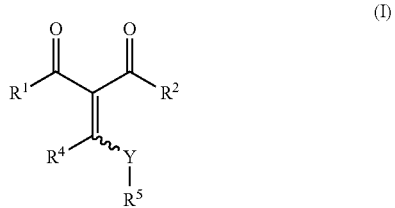

(I)

$R^1$ is selected from the group consisting of $CF_2Cl$, $CF_2H$, $CFCl_2$, $CFClH$, $CF_2Br$, $CCl_3$, $CF_3$, $CBr_3$, and $CI_3$. Preferably, $R^1$ is selected from the group consisting of $CF_2Cl$, $CF_2H$, $CFCl_2$, $CFClH$ and $CF_2Br$. More preferably, $R^1$ is selected from the group consisting of $CF_2Cl$, $CF_2H$, $CFCl_2$ and $CFClH$. Even more preferably, $R^1$ is selected from the group consisting of $CF_2Cl$ and $CF_2H$. In a most preferred aspect, $R^1$ is $CF_2H$.

$R^2$ is $CHal_3$ wherein Hal is a halogen and each Hal is selected independently; wherein, when $R^2$ is $CF_3$, $R^1$ contains two, one or zero fluorine atoms or, when $R^2$ is $CCl_3$, $R^1$ contains two, one or zero chlorine atoms; preferably, all the Hal in $CHal_3$ are the same Hal species; thus $CHal_3$ preferably is selected from the group consisting of $CCl_3$, $CF_3$, $CBr_3$, and $CI_3$; $R^2$ often is selected from the group consisting of $CCl_3$, $CF_3$, $CBr_3$, and $CI_3$; preferably, $R^2$ is selected from the group consisting of $CCl_3$, $CF_3$ and $CBr_3$. More preferably, $R^2$ is selected from the group consisting of $CCl_3$ and $CF_3$. In one very preferred aspect, $R^2$ is $CCl_3$. In another very preferred aspect, $R^2$ is $CF_3$.

Y is selected from the group consisting of S, O and $NR^6$, wherein O and $NR^6$ are preferred $R^4$ is selected from the group consisting of H, X', OR', SR', COOR', $C(O)NR'_2$, wherein R' are selected independently in $C(O)NR'_2$, wherein R' is hydrogen or a $C_1$-$C_{12}$-alkyl group, CN, $C_1$-$C_{12}$-alkyl, $C_2$-$C_6$ alkenyl, aryl, cycloalkyl, aralkyl, heteroaryl, each of which is optionally substituted by one or more groups selected from the group consisting of —R', —X', —OR', —SR', —NR'$_2$, —SiR'$_3$, —COOR', —(C—O)R', —CN and —CONR'$_2$, in which R' are selected independently, wherein R' is hydrogen or a $C_1$-$C_{12}$-alkyl group and X' is F, Cl, Br, or I; when $R^4$ is a $C_1$-$C_{12}$-alkyl group, methyl, ethyl, n-propyl, isopropyl, n-, iso-, sec- and t-butyl are preferred, and methyl and ethyl are most preferred;

$R^5$ and $R^6$ independently are selected from the group consisting of $C_1$-$C_{12}$-alkyl, $C_2$-$C_6$ alkenyl or $C_3$-$C_{10}$-cycloalkyl group, each of which is optionally substituted by one or more groups selected from the group consisting of —R', —X', —OR', —SR', —NR'$_2$, —SiR'$_3$, —COOR', —CN and —CONR'$_2$, wherein R' is hydrogen or a $C_1$-$C_{12}$-alkyl group, which is preferably selected from the group consisting of methyl, ethyl, n-propyl, isopropyl, n-, iso-, sec- and t-butyl, and X' is F, Cl, Br, or I, or, when $Y=NR^6$, $R^5$ together with $R^6$ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members.

In one particular aspect, Y is S, wherein $R^5$ is hydrogen or a $C_1$-$C_{12}$-alkyl group, preferably a $C_1$-$C_4$-alkyl-group.

For the purpose of the present invention, the definition $C_1$-$C_{12}$-alkyl comprises the largest range defined herein for an alkyl group. Specifically, this definition comprises, for example, the meanings methyl, ethyl, n-propyl, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl and n-dodecyl. Often, methyl, ethyl, n-propyl, isopropyl, n-, iso-, sec- and t-butyl are most preferred residues selected from the group $C_1$-$C_{12}$-alkyl.

The term "$C_3$-$C_{10}$-cycloalkyl", as used in this invention, denotes mono-, bi- or tricyclic hydrocarbon groups comprising 3 to 10 carbon atoms, especially 3 to 6 carbon atoms. Examples of monocyclic groups include cyclopropyl, cyclobutyl, cyclopentyl, cyclohexyl, cycloheptyl or cyclooctyl. Examples of bicyclic groups include bicyclo[2.2.1]heptyl, bicyclo[3.1.1]heptyl, bicyclo[2.2.2]octyl and bicyclo[3.2.1]octyl. Examples of tricyclic groups are adamantyl and homoadamantyl.

The term "$C_2$-$C_6$-alkenyl group" denotes a group comprising a carbon chain and at least one double bond. Alkenyl group are, for example, ethenyl, propenyl, butenyl, pentenyl or hexenyl.

In connection with the definition of the group —$NR^5R^6$, the term "5- to 10-membered heterocyclic radical" denotes a nitrogenous mono- or bicyclic group having 5, 6, 7, 8, 9 or 10 ring members, which is attached via the nitrogen atom to the remainder of the compound of the formula (I) or (II), which, in addition to the nitrogen atom, may have a further 1, 2 or 3 heteroatoms selected from the group consisting of O, N and S as ring members and which is unsubstituted or may have 1, 2 or 3 substituents. The substituents, provided they are attached to a carbon atom of the heterocyclic radical, are preferably selected from the group consisting of halogen, CN, $C_1$-$C_4$ alkyl, $C_1$-$C_4$-haloalkyl, $C_1$-$C_4$-alkoxy and $C_1$-$C_4$-haloalkoxy and, provided they are attached to a further nitrogen atom of the heterocyclic radical, are preferably selected from the group consisting of $C_1$-$C_4$-alkyl and $C_1$-$C_4$-haloalkyl. Examples of 5- to 10-membered heterocyclic radicals are pyrrol-1-yl, pyrrolidin-1-yl, oxazolidin-3-yl, thiazolidin-3-yl, imidazol-1-yl, imidazolin-1-yl, 3-methylimidazolin-1-yl, 3-ethylimidazolin-1-yl, 3-propylimidazolin-1-yl, 3-(1-methylethyl)imidazolin-1-yl, 3-butylimidazolin-1-yl, 3-(1,1-dimethylethyl)imidazolin-1-yl, pyrazol-1-yl, pyrazolin-1-yl, pyrazolidin-1-yl, 2-methylpyrazolidin-1-yl, 2-ethylpyrazolidin-1-yl, 2-propylpyrazolidin-1-yl, 2-(1-methylethyl)pyrazolidin-1-yl, 2-butylpyrazolidin-1-yl, 2-(1,1-dimethylethyl)pyrazolidin-1-yl, piperidin-1-yl, morpholin-4-yl, thiamorpholin-4-yl, piperazin-1-yl, 4-methylpiperazin-1-yl, 4-ethylpiperazin-1-yl, 4-propylpiperazin-1-yl, 4-(1-methylethyl)piperazin-1-yl, 4-butylpiperazin-1-yl, 4-(1,1-dimethylethyl)piperazin-1-yl, indol-1-yl, indolin-1-yl, isoindol-1-yl, isoindolin-1-yl, indazol-1-yl, indazolin-1-yl, 2-methylindazolin-1-yl, indazolin-2-yl and 1-methylindazolin-1-yl, where the heterocyclic groups mentioned above are unsubstituted, or 1, 2 or 3 of the ring carbon atoms carry a substituent selected from the group consisting of halogen, CN, nitro, $C_1$-$C_4$-alkyl, $C_1$-$C_4$-alkoxy and $C_1$-$C_4$-haloalkoxy. Preferred heterocyclic radicals are optionally substituted piperidinyl and optionally substituted morpholinyl.

In the context of the present invention, aryl groups are, unless defined otherwise, aromatic hydrocarbon groups which may contain one, two or more heteroatoms selected from the group consisting of O, N, P and S and which may optionally be substituted by further groups selected from the group consisting of R', —X', —OR', —SR', —NR'$_2$, —SiR'$_3$, —COOR', —(C—O)R', —CN and —CONR'$_2$, where R' and X' are defined as above.

In one aspect, the term "aryl" is a $C_5$-$C_{18}$-aryl. The term "$C_5$-$C_{18}$-aryl" denotes the largest range defined herein for an aryl groups having 5 to 18 skeleton atoms, where the carbon atoms may be replaced by heteroatoms, thus forming a heteroaryl. Specifically, this definition comprises, for example, the meanings cyclopentadienyl, phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In the context of the present invention, arylalkyl groups (aralkyl groups) are, unless defined otherwise, alkyl groups which are substituted by aryl groups, which may have a $C_{1-8}$-alkylene chain and which may be substituted in the aryl skeleton or the alkylene chain by one or more heteroatoms selected from the group consisting of O, N, P and S and optionally by further groups selected from the group consisting of R', —X', —OR', —SR', —NR'$_2$, —SiR'$_3$, —COOR', —(C—O)R', —CN and —CONR'$_2$, where R', which may further contain one or more heteroatoms selected from the group consisting of N, O, P and S, and X' are defined as above.

The definition $C_7$-$C_{19}$-aralkyl group comprises the largest range defined herein for an arylalkyl group having a total of 7 to 19 atoms in the skeleton and the alkylene chain. Specifically, this definition comprises, for example, the meanings benzyl and phenylethyl.

In the context of the present invention, alkylaryl groups (alkaryl groups) are, unless defined otherwise, aryl groups which are substituted by alkyl groups, which may have a $C_1$-$C_8$-alkylene chain and which may be substituted in the aryl skeleton or the alkylene chain by one or more heteroatoms selected from the groups consisting of O, N, P and S and optionally by further groups selected from the group consisting of R', —X', —OR', —SR', —NR'$_2$, —SiR'$_3$, —COOR', —(C—O)R', —CN and —CONR'$_2$, where R', which may further contain one or more heteroatoms selected from the group consisting of N, O, P and S, and X' are defined as above.

The definition $C_7$-$C_{19}$-alkylaryl group comprises the largest range defined herein for an alkylaryl group having a total of 7 to 19 atoms in the skeleton and the alkylene chain. Specifically, this definition comprises, for example, the meanings tolyl, 2,3-, 2,4-, 2,5-, 2,6-, 3,4- or 3,5-dimethylphenyl.

In a first preferred embodiment in relation to the compound of formula (I), Y is O, $R^1$ is $CF_2Cl$, $R^2$ is $CCl_3$, $R^4$ is H and $R^5$ is ethyl.

In a second preferred embodiment in relation to the compound of formula (I), Y is O, $R^1$ is $CF_2Cl$, $R^2$ is $CF_3$, $R^4$ is H and $R^5$ is ethyl.

In a third preferred embodiment in relation to the compound of formula (I), Y is O, $R^1$ is $CF_2H$, $R^2$ is $CCl_3$, $R^4$ is H are $R^5$ is ethyl.

In a fourth preferred embodiment in relation to the compound of formula (I), Y is O, $R^1$ is $CF_2H$, $R^2$ is $CF_3$, $R^4$ is H are $R^5$ is ethyl.

In a fifth preferred embodiment in relation to the compound of formula (I), Y is O, $R^1$ is $CF_2H$, $R^2$ is $CBr_3$, $R^4$ is H and $R^5$ is ethyl.

In a sixth preferred embodiment in relation to the compound of formula (I), Y is O, $R^1$ is $CF_2Cl$, $R^2$ is $CF_3$, $R^4$ is H and $R^5$ is ethyl.

In a seventh preferred embodiment in relation to the compound of formula (I), Y is $NR^6$, $R^1$ is $CF_2Cl$, $R^2$ is $CCl_3$, $R^4$ is H and $R^5$ and $R^6$ are $CH_3$.

In an eighth preferred embodiment in relation to the compound of formula (I), Y is $NR^6$, $R^1$ is $CF_2Cl$, $R^2$ is $CF_3$, $R^4$ is H and $R^5$ and $R^6$ are $CH_3$.

In a ninth preferred embodiment in relation to the compound of formula (I), Y is $NR^6$, $R^1$ is $CF_2H$, $R^2$ is $CCl_3$, $R^4$ is H and are $R^5$ and $R^6$ are $CH_3$.

In a tenth preferred embodiment in relation to the compound of formula (I), Y is $NR^6$, $R^1$ is $CF_2H$, $R^2$ is $CF_3$, $R^4$ is H are $R^5$ and $R^6$ are $CH_3$.

In an eleventh preferred embodiment in relation to the compound of formula (I), Y is $NR^6$, $R^1$ is $CF_2H$, $R^2$ is $CBr_3$, $R^4$ is H and $R^5$ and $R^6$ are $CH_3$.

In a twelfth preferred embodiment in relation to the compound of formula (I), Y is $NR^6$, $R^1$ is $CF_2Cl$, $R^2$ is $CF_3$, $R^4$ is H and $R^5$ and $R^6$ are $CH_3$.

In a thirteenth preferred embodiment in relation to the compound of formula (I), Y is O, $R^1$ is $CF_3$, $R^2$ is $CCl_3$, $R^4$ is H and $R^5$ is ethyl.

In a fourteenth preferred embodiment in relation to the compound of formula (I), Y is $NR^6$, $R^1$ is $CF_3$, $R^2$ is $CCl_3$, $R^4$ is H and $R^5$ and $R^6$ are $CH_3$.

In a fifteenth preferred embodiment in relation to the compound of formula (I), one methyl group $R^5$ of embodiments seven to twelve is replaced by $C_2$-$C_{12}$-alkyl, $C_3$-$C_{10}$-cycloalkyl, aryl or aralkyl.

In a sixteenth preferred embodiment in relation to the compound of formula (I), the other methyl group in $R^6$ of embodiment thirteen is replaced by $C_2$-$C_{12}$-alkyl, $C_3$-$C_{10}$-cycloalkyl, aryl or aralkyl.

In a seventeenth preferred embodiment in relation to the compound of formula (I), the ethyl group $R^5$ of the first to sixth or thirteenth preferred embodiment in relation to the compound of formula (I), is replaced by methyl, $C_3$-$C_{12}$-alkyl, $C_3$-$C_{10}$-cycloalkyl, aryl or aralkyl.

In an eighteenth preferred embodiment in relation to the compound of formula (I), the ethyl group $R^5$ of the first to sixth or thirteenth preferred embodiment in relation to the compound of formula (I), is replaced by methyl, $C_3$-$C_{12}$-alkyl, $C_3$-$C_{10}$-cycloalkyl, aryl or aralkyl.

In a nineteenth preferred embodiment in relation to the compound of formula (I), $R^5$ and $R^6$ of the seventh to seventeenth preferred embodiment in relation to the compound of formula (I), together with the nitrogen atom to which the two radicals are attached, are an optionally substituted 5- to 10-membered heterocyclic radical which, in addition to the nitrogen atom, can contain a further 1, 2 or 3 heteroatoms selected from the group consisting of O, N and S as ring members.

The above preferred residues Y, $R^1$, $R^2$, $R^4$, $R^5$ and $R^6$ also apply to the other compounds of the present invention, in particular to (II), (VII), (XIII), (IVa), (IVb), (IX) and (XII).

The compounds of formula (I) have been found to be particularly useful as starting materials or intermediates in the manufacture of compound of formula (II) or (VII), which are valuable intermediates for the manufacture of agrochemical or pharmaceutical active ingredients. When reacted with a compound of formula (III), (VIII) or (V), the —C(O)$R^2$ group can, for example, be simultaneously with the cyclization converted into a C(O)O$R^{10}$ group under the reaction conditions required for the cyclization. In one preferred aspect, the reaction is carried out in the presence of at least one base other than (III), (VIII) and (V). Compound (II) can also be obtained by cyclization of (I) to (VII), with subsequent conversion of the C(O)$R^2$ group into the COO$R^{10}$ group as will be explained later. The compounds of formula (VII) can also be converted into compounds of formula (IX), as will be explained later.

The invention concerns thus a process for manufacturing a compound according to formula (II)

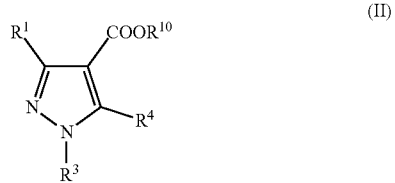

(II)

which comprises the step of reacting a compound of formula (I) with a compound of formula (III), (VIII) or (V)

(III)

(VIII)

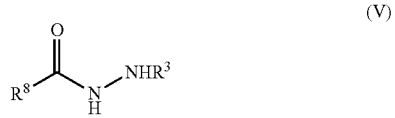

(V)

wherein $R^3$ in (III) and (V) is, or $R^3$, $R^{3'}$ and $R^{3''}$ independently from each other in (VIII) are, selected from the group consisting of $C_1$-$C_{12}$-alkyl, $C_2$-$C_6$ alkenyl, cycloalkyl, aryl, heteroaryl, aralkyl, and, for $R^{3'}$ and $R^{3''}$, H, each of which is optionally substituted by one or more groups selected from the group consisting of —R', —X', —OR', —SR', —NR'$_2$, —SiR'$_3$, —COOR'', —CN and —CONR'$_2$, where R' is hydrogen or a $C_1$-$C_{12}$-alkyl group which are the same or different in —CONR'$_2$, and X' is F, Cl, Br, or I;

$R^{10}$ is selected from the group consisting of H, $C_1$-$C_{12}$-alkyl, $C_2$-$C_6$ alkenyl or $C_3$-$C_8$-cycloalkyl group, each of which is optionally substituted by one or more groups selected from the group consisting of —R', —X', —OR', —SR', —NR'$_2$, —SiR'$_3$, —COOR', —(C=O)R', —CN and —CONR'$_2$, where R' is hydrogen or a $C_1$-$C_{12}$-alkyl group which are the same or different in —CONR'$_2$, and X' is F, Cl, Br, or I, wherein it is preferred that $R^{10}$ is selected from H and $C_1$-$C_4$-alkyl, and $R^{10}$=H is most preferred;
and wherein (I) is as defined as above.

The N-alkylhydrazones of the formula (VIII) have been described in the literature (Zhurnal Organicheskoi Khimii (1968), 4(6), 986-92) and can be obtained by reacting commercially available hydrazines of the formula (III) with carbonyl compounds of the formula $R^{3'}R^{3''}C=O$.

$R^8$ is selected from the group consisting of $R^9$, wherein $R^9$ denotes $C_1$-$C_{12}$-alkyl, O$R^9$ and N$R^{11}R^{11'}$, wherein $R^{11}$ and $R^{11'}$ independently are selected from the group consisting of $C_1$-$C_{12}$-alkyl and H. Compounds of formula (V) have been described in WO2015097658, which is hereby incorporated by reference for all purposes.

The compound of formula (III) and (VIII) are preferred in the manufacture of compound (II) from compound (I).

In one other preferred aspect, compound of formula (VIII) is preferred in the manufacture of compound (II), (VII) and/or (IX) from compound (I). The use of compound (VIII) in the manufacture of (II), (VII) and/or (IX) from compound (I) can result in an improved regioselectivity in the cyclization to obtain (II), (VII) and/or (IX). As stated above, $R^{3'}$ and $R^{3''}$ in formula (VIII) are independently selected from the group consisting of $C_1$-$C_{12}$-alkyl, $C_2$-$C_6$ alkenyl, cycloalkyl, aryl, heteroaryl, aralkyl and H. In a preferred aspect, $R^{3'}$ is H and $R^{3''}$ is selected from the group consisting of $C_1$-$C_{12}$-alkyl, $C_2$-$C_6$ alkenyl, cycloalkyl, aryl, heteroaryl, aralkyl, wherein methyl, ethyl, i-prop, and aryl is preferred, and aryl=benzene is more preferred. In one aspect, the aryl, preferably benzene, residue is optionally substituted, preferably by one or more groups of N$R^{3'}R^{3''}$, wherein NH$_2$ is preferred, for example in p-position to the attachment position of the C-atom in 3-Position of (VIII). The p-aminobenzaldehyde which is released during the reaction of (VIII) with (I) can easily be recovered by acidic/basic extraction methods for convenient recycling. When compound of formula (VIII) is preferred in the manufacture of compound (II), (VII) and/or (IX) from compound (I), the reaction between (VIII) and (I) preferably is carried out in the presence of a catalyst, more preferably an acidic catalyst. Suitable catalysts are, for example, $CH_3COOH$, $CF_3COOH$, $KHSO_4$, $H_2SO_4$, $NaHSO_4$ and HCl. The catalyst can be employed in up to stoichiometric amounts in relation to compound (I), such as 0.95 or 1 eq.

In another preferred aspect, the reaction between (VIII) and (I) preferably is carried out in the absence of a catalyst.

When a compound of formula (VIII) is reacted with (I), a desired intermediate (XIV) generally forms, as described below. When (XIV) is contacted with an acid, as described below, generally a compound of formula $R^{3'}R^{3''}C(O)$ is released. The compound, for example benzaldehyde, can be removed from the reaction mixture, for example by extraction or, preferably, distillation such as falling film distillation. The compound of formula R³'R³''C(O) can also be removed after the intermediate is contacted with the acid and base to obtain a compound of formula (XIII). In this case, R³'R³''C(O) can be removed, for example, by organic extraction of the aqueous phase containing (XIII) R³'R³''C(O) can thus be effectively recycled.

In a first preferred embodiment in relation to the manufacture of the compound of formula (II) from a compound of formula (I), Y is O, $R^1$ is $CF_2Cl$, $R^2$ is $CCl_3$, $R^4$ is H and $R^5$ is ethyl in the compound of formula (I).

In a second preferred embodiment in relation to the manufacture of the compound of formula (II) from a compound of formula (I), Y is O, $R^1$ is $CF_2Cl$, $R^2$ is $CF_3$, $R^4$ is H and $R^5$ is ethyl in the compound of formula (I).

In a third preferred embodiment in relation to the manufacture of the compound of formula (II) from a compound of formula (I), Y is O, $R^1$ is $CF_2H$, $R^2$ is $CCl_3$, $R^4$ is H are $R^5$ is ethyl in the compound of formula (I).

In a fourth preferred embodiment in relation to the manufacture of the compound of formula (II) from a compound of formula (I), Y is O, $R^1$ is $CF_2H$, $R^2$ is $CF_3$, $R^4$ is H are $R^5$ is ethyl in the compound of formula (I).

In a fifth preferred embodiment in relation to the manufacture of the compound of formula (II) from a compound of formula (I), Y is O, $R^1$ is $CF_2H$, $R^2$ is $CBr_3$, $R^4$ is H and $R^5$ is ethyl in the compound of formula (I).

In a sixth preferred embodiment in relation to the manufacture of the compound of formula (II) from a compound of formula (I), Y is O, $R^1$ is $CF_2Cl$, $R^2$ is $CF_3$, $R^4$ is H and $R^5$ is ethyl in the compound of formula (I).

In a seventh preferred embodiment in relation to the manufacture of the compound of formula (II) from a compound of formula (I), Y is O, $R^1$ is $CF_3$, $R^2$ is $CCl_3$, $R^4$ is H and $R^5$ is ethyl in the compound of formula (I).

In the abovementioned preferred embodiments in relation to the manufacture of the compound of formula (II) from a compound of formula (I), $R^3$ in the compound of formula (III) preferably is Methyl.

In an eighth preferred in relation to the manufacture of the compound of formula (II) from a compound of formula (I), Y is $NR^6$, $R^1$ is $CF_2Cl$, $R^2$ is $CCl_3$, $R^4$ is H and $R^5$ and $R^6$ are $CH_3$.

In a ninth preferred in relation to the manufacture of the compound of formula (II) from a compound of formula (I), Y is $NR^6$, $R^1$ is $CF_2Cl$, $R^2$ is $CF_3$, $R^4$ is H and $R^5$ and $R^6$ are $CH_3$.

In a tenth preferred in relation to the manufacture of the compound of formula (II) from a compound of formula (I), Y is $NR^6$, $R^1$ is $CF_2H$, $R^2$ is $CCl_3$, $R^4$ is H are $R^5$ and $R^6$ are $CH_3$.

In an eleventh preferred embodiment in relation to the manufacture of the compound of formula (II) from a compound of formula (I), Y is $NR^6$, $R^1$ is $CF_2H$, $R^2$ is $CF_3$, $R^4$ is H are $R^5$ and $R^6$ are $CH_3$.

In a twelfth preferred embodiment in relation to the manufacture of the compound of formula (II) from a compound of formula (I), Y is $NR^6$, $R^1$ is $CF_2H$, $R^2$ is $CBr_3$, $R^4$ is H and $R^5$ and $R^6$ are $CH_3$.

In a thirteenth preferred in relation to the manufacture of the compound of formula (II) from a compound of formula (I), Y is $NR^6$, $R^1$ is $CF_2Cl$, $R^2$ is $CF_3$, $R^4$ is H and $R^5$ and $R^6$ are $CH_3$.

In a fourteenth preferred in relation to the manufacture of the compound of formula (II) from a compound of formula (I), Y is $NR^6$, $R^1$ is $CF_3$, $R^2$ is $CCl_3$, $R^4$ is H and $R^5$ and $R^6$ are $CH_3$.

In a fifteenth preferred embodiment in relation to the manufacture of the compound of formula (II) from a compound of formula (I), one methyl group $R^5$ in (I) of embodiments eight to fourteen is replaced by $C_2$-$C_{12}$-alkyl, $C_3$-$C_{10}$-cycloalkyl, aryl or aralkyl.

In a sixteenth preferred embodiment in relation to the manufacture of the compound of formula (II) from a compound of formula (I), the other methyl group $R^6$ of embodiment fifteen is replaced by $C_2$-$C_{12}$-alkyl, $C_3$-$C_{10}$-cycloalkyl, aryl or aralkyl.

In a seventeenth preferred embodiment in relation to the manufacture of the compound of formula (II) from a compound of formula (I), the ethyl group $R^5$ of the first to sixth preferred embodiment in relation to the manufacture of the compound of formula (II) from a compound of formula (I), is replaced by methyl, $C_3$-$C_{12}$-alkyl, $C_3$-$C_{10}$-cycloalkyl, aryl or aralkyl.

In an eighteenth preferred embodiment in relation to the manufacture of the compound of formula (II) from a compound of formula (I), $R^5$ and $R^6$ of the eight to seventeenth preferred embodiment in relation to the manufacture of the compound of formula (II) from a compound of formula (I), together with the nitrogen atom to which the two radicals are attached, are an optionally substituted 5- to 10-membered heterocyclic radical which, in addition to the nitrogen atom, may contain a further 1, 2 or 3 heteroatoms selected from the group consisting of O, N and S as ring members.

The above preferred residues of the preferred embodiments in relation to the manufacture of the compound of formula (II) from a compound of formula (I), such as Y, $R^1$, $R^2$, $R^4$, $R^5$ and $R^6$, also apply to the other compounds of the present invention, in particular to (I), (VII), (XIII), (IVa), (IVb), (IX) and (XII), and the manufacture of any of those compounds from (II) or (I).

In the process according to the present invention, the compound of formula (III), (VIII) or (V) is often used in an amount of equal to or greater than 0.8 mol, preferably equal to or greater than 0.9 mol and more preferably equal to or greater than 0.95 mol based on 1 mol of formula (I). Often, the compound of formula (III), (VIII) or (V) is used in an amount of equal to or less than 1.2 mol, preferably equal to or less than 1.1 mol and more preferably equal to or less than 1.05 mol based on 1 mol of formula (I). In one aspect, Compound (III) is preferred.

The compound of formula (III) or (V), preferably (III), can also be employed in its hydrate form, or in a salt, more particularly a halide, form. In another aspect, the compound of formula (III) is used in its anhydrous form. In yet still another aspect, the compound of formula (III) is used as aqueous solution, or in a mixture of a solvent and water. This often has the advantage that the formula (III) is provided in a less hazardous form.

When a compound of formula (I) is reacted with a compound of formula (VIII), generally an intermediate of formula (XIV) forms as a desired intermediate.

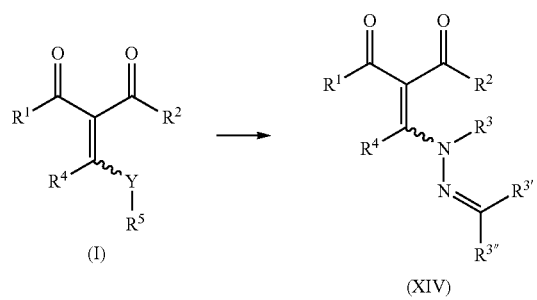

In one embodiment, the process comprises further a step of acidic treatment of the intermediate (XIV) formed by the reaction of (I) with (VIII) or of the intermediate formed by the reaction of (I) with (V). Formation of (XIV) by reaction of (I) with (VIII) is preferred, in particular when Y=NR$^6$. "Acidic treatment" denotes the addition of an acid, which can be aqueous or non aqueous, to the intermediate. Non-aqueous acids can be, for example, HCl, H$_2$SO$_4$ or Lewis Acids such as AlCl$_3$. Aqueous acids can be, for example, aq. H$_2$SO$_4$ or aq. HCl, preferably aq. HCl. NaHSO$_4$ can also be used as an acid. Often, catalytically amounts of acid, for example, 1 mol % of acid in relation to compound (I), are sufficient to effect cyclization of the intermediate, should the cyclization not have been effected or not fully been effected by the reaction between (I) and (VIII) or (V). Higher amounts of acid, such as from 1 to 100 mol %, can also be used for effecting the cyclization.

The invention relates also to a compound of formula (XIV), wherein wherein R$^1$, R$^2$, R$^4$, R$^3$, R$^3$' and R$^3$" are defined as before, and the use of a compound of formula (XIV) for the manufacture of a compound of formula (II), (VII) or (XIII), and/or the use of a compound of formula (XIV) for the manufacture of an agrochemically or pharmaceutically active compound. Preferred compounds of formula (XIV) are given in table 1.

TABLE 1

Preferred compounds of formula (VIX)

| | R$^1$ | R$^2$ | R$^3$ | R$^3$' | R$^3$" | R$^4$ |
|---|---|---|---|---|---|---|
| (VIX).1 | CHF$_2$ | CCl$_3$ | CH$_3$ | H | Phenyl | H |
| (VIX).2 | CClF$_2$ | CCl$_3$ | CH$_3$ | H | Phenyl | H |
| (VIX).3 | CF$_3$ | CCl$_3$ | CH$_3$ | H | Phenyl | H |
| (VIX).4 | CHF$_2$ | CF$_3$ | CH$_3$ | H | Phenyl | H |
| (VIX).5 | CClF$_2$ | CF$_3$ | CH$_3$ | H | Phenyl | H |
| (VIX).6 | CCl$_3$ | CF$_3$ | CH$_3$ | H | Phenyl | H |
| (VIX).7 | CHF$_2$ | CBr$_3$ | CH$_3$ | H | Phenyl | H |
| (VIX).8 | CClF$_2$ | CBr$_3$ | CH$_3$ | H | Phenyl | H |
| (VIX).9 | CF$_3$ | CBr$_3$ | CH$_3$ | H | Phenyl | H |

When the reaction is performed in the presence of water, the water content in the reaction mixture generally is equal to or greater than 0.1 wt %, preferably equal to or greater than 1 wt % and more preferably equal to or greater than 5 wt %. Often, the water content is equal to or less than 50 wt %, preferably equal to or less than 40 wt % and more preferably equal to or less than 30 wt %. The weight percentage relates to the weight percentage in relation to the reaction mixture. This relates to the reaction of (I) with (III), (VIII) or (V).

When the reaction is performed in the presence of water, the reaction is often performed at a temperature which generally is equal to or greater than −80° C., preferably equal to or greater than −50° C. and more preferably equal to or greater than −20° C. Often, the temperature, when the reaction is performed in the presence of water, is equal to or less than 100° C., preferably equal to or less than 50° C. and more preferably equal to or less than 20° C.

When (XIV) is contacted with an acid to obtain a compound of formula (VII) as described above, essentially anhydrous reaction can be preferred. The reaction can be performed at ambient temperature, i.a. from 20 to 25° C. Preferably, the reaction is performed at elevated temperatures. Often, the temperature is from equal to or more than 30° C., preferably equal to or more than 50° C., more preferably equal to or more than 70° C., and even more preferably equal to or more than 90° C. Generally, the temperature is equal to or less than 200° C., preferably equal to or less than 190° C. and more preferably equal to or less than 180° C. It is often advantageous to heat the reaction mixture to the desired reaction temperature in a time of from 10 seconds to 30 minutes after (XIV) is contacted with the acid. Times of equal to or less than 15 minutes, preferably equal to or less than 10 minutes, and preferably equal to or less than 5 minutes generally are appropriate. Often, times of equal to or more than 10 seconds, equal to than 30 seconds or equal to or more than 60 seconds are appropriate. Conducting the reaction at higher temperatures which are heated to the temperature in the given time can improve regio selectivity when the compound of formula (VII) is formed. The amount of acid used in this reaction can be dependent on the acid strength, and often is from 1 to 100 mol % or compound (XIV). The amount of acid often is equal to or more than 1 mol %, equal to or more than 10 mol %, equal to or more than 25 mol %, equal to or more than 50 mol %, or even equal to or more than 100 mol %. In aspect, the acid can even be used in an excess, for example as solvent of the reaction.

The reaction of the compound of the formula (I) with the compound (III), (VIII) or (V), preferably (III) or (VIII), is often carried out such that the compound of the formula (III), (VIII) or (V) is initially charged in a suitable solvent, the desired reaction temperature is set and the compound of the formula (I), if appropriate in the form of a solution and/or a reaction mixture obtained during a previous reaction step, is then added. In one aspect, the compound of formula (I) is in the form of a crude solution obtained by the previous step in which the compound of formula (I) is formed.

In another aspect, the compound of formula (I), optionally as solution in an appropriate solvent, is initially charged, the desired reaction temperature is set and the compound of the formula (III), (VIII) or (V), preferably (V), if appropriate in the form of a solution and/or a reaction mixture obtained during the provision, is then added. In one aspect, the compound of formula (I) is in the form of a crude solution obtained by the previous step in which the compound of formula (I) is formed.

In the reaction of the compound of the formula (I) with the compound (III), (VIII) or (V), preferably (III) or (VIII), can also carried out such that the compound of the formula (III), (VIII) or (V) is charged into the reaction mixture and/or solvent simultaneous with compound (I).

Appropriate solvents suitable for reacting the compound of the formula (I) with the compound (III), (VIII) or (V), preferably (III) or (VIII), are, for example, protic polar solvents, such as aliphatic alcohols having preferably 1 to 4 carbon atoms, especially methanol, ethanol, n-propanol, isopropanol, n-butanol, isobutanol or tert-butanol, wherein ethanol is preferred, nonpolar aprotic solvents, e.g. aromatic hydrocarbons, such as benzene, toluene, xylenes, mesitylene, cumene, chlorobenzene, nitrobenzene or tert-butylbenzene, aprotic polar solvents, such as cyclic or acyclic ethers, especially diethyl ether, tert-butyl methyl ether (MTBE), cyclopentyl methyl ether, tetrahydrofuran (THF) or dioxane, cyclic or acyclic amides, especially dimethylformamide, dimethylacetamide, N-methylpyrrolidone, ureas, such as N,N'-dimethyl-N,N'-ethyleneurea (DMEU), N,N'-dimethyl-N,N'-propyleneurea (DMPU) or tetramethylurea, or aliphatic nitriles, especially acetonitrile or propionitrile, or mixtures of the solvents mentioned above. In one aspect, the solvent is essentially anhydrous. When an alcohol of formula R$^{10}$—OH is present, a compound of formula (II) wherein R$^{10}$ is the same as in R$^{10}$—OH can be obtained, in particular when a base is present. In one particular aspect, the reaction of preparing (II) or (VII) are performed in the presence of a solvent R³R³''C(O), which can enhance the regioselectivity of the cyclization.

In another aspect, the solvent can comprise water.

When an intermediate of formula (XIV) is obtained, the intermediate can be isolated or used as crude intermediate. When the intermediate is isolated, generally this can be effected by removal of any solvents present, and optionally at least one of the steps of crystallization, distillation, in particular thin film distillation, chromatography and sublimation. In one preferred aspect, the reaction of the compound of the formula (I) with the compound (III), (VIII) or (V), preferably (III), can, if appropriate, be carried out in the presence of at least one base. In one aspect, the presence of a base is preferred. The term "base" denotes a base which is not (III), (VIII) or (V). Bases suitable for this purpose are organic bases, for example the abovementioned acyclic tertiary amines, such as trimethylamine, triethylamine, diisopropylethylamine, tert-butyldimethylamine or ethyldicyclohexylamine, the abovementioned cyclic tertiary amines, such as N-methylpyrrolidine, N-methylpiperidine, N-methylmorpholine, N,N'-dimethylpiperazine, pyridine, collidine, lutidine or 4-dimethylaminopyridine, or bicyclic amines, such as diazabicycloundecene (DBU) or diazabicyclononene (DBN). Trimethylamine, triethylamine, diisopropylethylamine are preferred, and trimethylamine is particularly preferred. Also suitable as bases are inorganic compounds, for example alkali metal and alkaline earth metal hydroxides, such as sodium hydroxide, potassium hydroxide or calcium hydroxide, alkali metal and alkaline earth metal oxides, such as lithium oxide, sodium oxide, calcium oxide or magnesium oxide, alkali metal and alkaline earth metal carbonates, such as lithium carbonate or calcium carbonate, alkali metal bicarbonates, such as sodium bicarbonate, alkali metal and alkaline earth metal hydrides, such as lithium hydride, sodium hydride, potassium hydride or calcium hydride, or alkali metal amides, such as lithium amide, sodium amide or potassium amide. Suitable bases are also alcoholates. When an alcoholate of the formula $M^xOR^{10}$ or $M^y(OR^{10})_2$ is present, a compound of formula (II) wherein $R^{10}$ is the same as in $M^xOR^{10}$ or $M^y(OR^{10})_2$ can be obtained. $M^x$ intends to denote a monobasic metal ion, such as an alkali metal ion, in particular sodium or potassium. $M^y$ intends to denote a dibasic metal ion, such as an earth alkali metal ion, in particular Sr, Ca or Ba.

In the process according to the present invention, the base, when present in the reaction between compound (I) and (III), (VIII) or (V), preferably (III), is often used in an amount of equal to or greater than 0.8 mol, preferably equal to or greater than 0.9 mol and more preferably equal to or greater than 0.95 mol based on 1 mol of formula (I). Often, the base is used in an amount of equal to or less than 1.2 mol, preferably equal to or less than 1.1 mol and more preferably equal to or less than 1.05 mol based on 1 mol of formula (I). In another aspect, the base can be used in catalytic amounts, based on the compound (I), for example in an amount of from about 0.001 to 0.2 mol per mole of the compound (I). However, the base may also be employed in a large excess based on the compound of the formula (I), for example as solvent, or the excess of base can be calculated on basis of (I) when the base contains $R^{10}$ in addition to its amount as catalytic or equimolar auxiliary.

If the reaction of the compound of the formula (I) and formula (III), (VIII) or (V), preferably (III), is carried out in the presence of water and a base, in one aspect, the base is preferably selected from the inorganic compounds mentioned above, specifically from the alkali metal or alkaline earth metal bases mentioned above and in particular from alkali metal hydroxides or alkaline earth metal hydroxides, such as NaOH or KOH. In another aspect, the base is selected from the group consisting of alcoholates and tertiary and secondary amines. With respect to the amounts used, the amounts disclosed above apply.

In a one aspect of the process according to the invention for preparing compounds of the formula (II), (VII) or (IX), the reaction of the compound of the formula (I) with the compound of the formula (III), (VIII) or (V), preferably (III), and more preferably (VIII), is carried out essentially anhydrously.

For the present invention, the term «essentially anhydrous» in intended to denote that a solvent, reagent, reaction mixture and/or additive has a water content of less than 500 ppm and in particular of less than 100 ppm. The water released during the or any reaction is not taken into account in the stated water content.

When the reaction is carried essentially anhydrously, the reaction is often performed at a temperature which generally is equal to or greater than −80° C., preferably equal to or greater than −60° C. and more preferably equal to or greater than −10° C. Often, the temperature, when the reaction is performed in the presence of water, is equal to or less than 100° C., preferably equal to or less than 60° C. and more preferably equal to or less than 40° C.

If the reaction of the compound of the formula (I) and formula (III), (VIII) or (V), preferably (III), is carried essentially anhydrously, in one aspect, the base is preferably selected from among alkaline earth metal and alkali metal carbonates and the organic bases mentioned above, in particular from among the organic bases and specifically from among the pyridines and acyclic tertiary amines mentioned above, such as pyridine or triethylamine. In another aspect, the base is an alcoholate. With respect to the amount employed, what was said above applies.

Compound (II) can be present in the form of a carboxylate (XIII). In one aspect, compound (II) can be present in the form of a carboxylate (XIII) after the step of reacting a compound of formula (I) with a compound of formula (III), (VIII) or (V). This can in particular be the case when a base is present in the process for the manufacture of (II) from (I) by reacting a compound of formula (I) with a compound of formula (III), (VIII) or (V), or when a base is added to the reaction product after that step, or when a base is added to the reaction mixture after cyclization of any intermediate formed by the reaction between a compound of formula (I) with a compound of formula (III), (VIII) or (V).

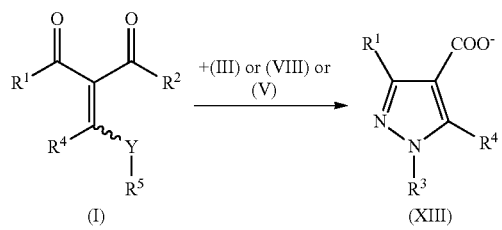

The counterion of the carboxylate (XIII) can preferably be the basic cation W corresponding to the base present in the reaction by reacting a compound of formula (I) with a compound of formula (III), (VIII) or (V), or the base added after that step, for example the alkali metal and alkaline earth metal cation if alkali metal and alkaline earth metal hydroxides are used as base. In particular, the cation B⁻ can be selected from the group $Na^+$, $K^+$, $Li^+$, $Ca^{2+}$, and $Mg^{2+}$, wherein $K^+$ and $Na^+$ are preferred. The cation can also be the cation of an organic base, such as quaternary ammonium cations or cations of formula $NR^{43}{}_3H^+$ wherein each $R^{43}$ independently is H or an organic radical, for example selected from methyl, ethyl, n- or i-propyl or i-, n- or tert-butyl.

The process for manufacturing compound (II) from (I) can comprise the step of acidification of a reaction mixture comprising carboxylate (XIII) in order to obtain the free carboxylic acid (II) with $R^{10}$=H. The acidification is achieved by addition of suitable acids, in particular aqueous acids, which may be inorganic, such as HCl, $H_2SO_4$ or $HNO_3$, or organic, such as citric acid. The term "acidification" generally denotes the adjustment of the pH of the reaction mixture by addition of the acid to values of equal to or lower than pH 7, and preferably equal to or less than pH 5. "Acidification" generally denotes the adjustment of the pH value to a value of equal to or greater than 1. For example, a pH value of from 1 to 2 can be suitable.

Work-up of the reaction mixtures obtained and isolation of the compound of the formula (II) is carried out in a customary manner, for instance by removing the solvent, for example under reduced pressure, by aqueous extractive work-up or by a combination of these measures. Further purification may be carried out, for example, by crystallization or by chromatography. Frequently, the product is already obtained in a purity which makes further purification steps redundant.

In one embodiment of the present invention, the process for the manufacture of a compound of formula (II) comprises a step of reductive dehalogenation, where $R^1$ is $R^{1'}$ is $CF_2Cl$ before the reductive dehalogenation step and $R^1$ is $R^{1''}$ is $CHF_2$ after the reductive dehalogenation step. In one aspect, in the compound of formula (I), $R^1$ is $R^{1'}$ is $CClF_2$, compound (I) is reacted with the compound of formula (III) to form the compound of formula (II) in which $R^1$ is $R^{1'}$ is $CClF_2$; subsequently, the compound of formula (II) is submitted to a step of reductive dehalogenation to form the compound of formula (II) in which $R^1$ is $R^{1''}$ is $CHF_2$. For such a step, the reaction conditions and reagents are described WO2012010692, which is hereby incorporated by reference for all purposes, as disclosed for the reductive dehalogenation for the compound of formula (II) therein.

In another embodiment of the present invention, the process for the manufacture of a compound of formula (II) comprises a step of reductive dehalogenation, where $R^1$ is $R^1$ is $CF_2Cl$ before the reductive dehalogenation step and $R^1$ is $R^{1''}$ is $CHF_2$ after the reductive dehalogenation step, wherein in the compound of formula (I) $R^1$ is $R^{1'}$ is $CClF_2$, the compound of formula (I) is submitted to a step of reductive dehalogenation to form the compound of formula (I) in which $R^1$ is $R^{1''}$ is $CHF_2$. Subsequently, the compound of formula (I) in which $R^1$ is $R^{1''}$ is $CHF_2$ is reacted with the compound of formula (III) to form the compound of formula (II) in which $R^1$ is $CClF_2$. For such a step, the reaction conditions and reagents can be taken from WO2012010692, which is hereby incorporated by reference for all purposes, as disclosed for the reductive dehalogenation for the compound of formula (II) therein, or alternatively from WO2009021987, which is hereby incorporated by reference for all purposes, as disclosed for the reductive dehalogenation for the esterified ketene adduct of RCFClC(O)Cl disclosed therein.

In one embodiment of the present invention, the process for manufacturing a compound of formula (II) which comprises a step of reacting a compound of formula (I) and (III), (VIII) or (V), preferably (III), further comprises a step of manufacturing the compound of formula (I). In one aspect, the step of manufacturing compound (I) comprises reacting a compound of formula (IVa) with a compound of formula (Va) or (Vb) to obtain compound (I)

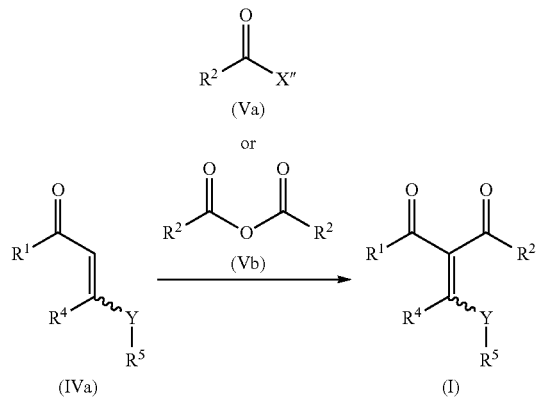

In another aspect, the step of manufacturing compound (I) comprises reacting a compound of formula (IVb) with a compound of formula (Vc) or (Vd) to obtain compound (I).

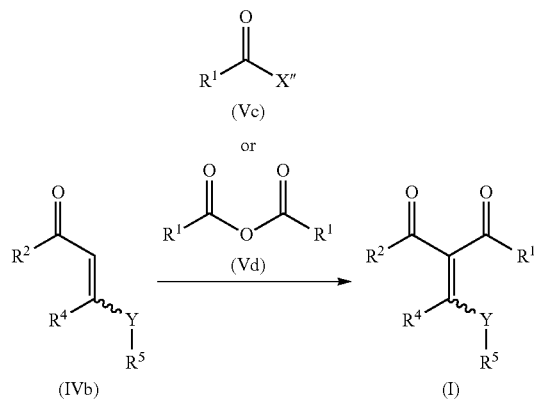

In above embodiment, Y, $R^5$ and $R^6$, if Y=$NR^6$, are defined as for (I) above. X" is selected from the group consisting of F, Cl, Br and I. Preferably, X" is F or Cl. In some aspects, which may depend on stability, reactivity, availability and its physical properties under the reaction conditions, F is preferred as X". In other cases, it is preferred that Cl is X". $R^1$, $R^4$ and $R^2$ are defined as already disclosed above for the compound of formula (I).

The compounds of formula Va and Vc are known to be carboxylic acid halides. Many compounds falling under the formula Va and Vc are well established and commercially available. The manufacture of difluoroacetyl fluoride is, for example, disclosed in EP694523 and U.S. Pat. No. 5,905,169 which are hereby incorporated by reference for all purposes. The manufacture of difluorochloroacetyl chloride is, for example, disclosed in U.S. Pat. Nos. 5,545,298 or 5,569,782, which are hereby incorporated by reference for all purposes, as well as the manufacture of trifluoroacetylchloride. The manufacture of halogenated carboxylic acid anhydrides such as Vb and Vd is known, for example, from WO2014195929, which is hereby incorporated by reference for all purposes. In one aspect, a compound of formula (IVe) $R^1$—C(O)—O—C(O)—$R^2$ can also be used for the manufacture of compound (I). The manufacture of mixed anhydrides is described, for example, in WO200117939, which is hereby incorporated by reference for all purposes, and can by also applied to compounds of formula (IVe).

The step to manufacture compound (I) from compound (IVa) or (IVb) generally is performed in the presence of a suitable solvent or a mixture of suitable solvents. Suitable solvents are, for example, nonpolar aprotic solvents, for example aromatic hydrocarbons, such as benzene, toluene, xylenes, or (cyclo)aliphatic hydrocarbons, such as hexane, cyclohexane and the like, and also mixtures of the solvents mentioned above. Examples of suitable organic solvents are likewise aprotic polar solvents, for example cyclic and acyclic ethers, such as diethyl ether, tert-butyl methyl ether (MTBE), diisopropyl ether, cyclopentyl methyl ether, tetrahydrofuran (THF) or dioxane, cyclic or acyclic amides, such as dimethyl formamide, dimethyl acetamide, N-methylpyrrolidone, ureas, such as N,N'-dimethyl-N,N'-ethyleneurea (DMEU), N,N'-dimethyl-N,N'-propyleneurea (DMPU) or tetramethylurea, or aliphatic nitriles, such as acetonitrile or propionitrile. Halogenated hydrocarbon solvents, such as chloroform or dichloromethane, can also be suitable solvents. Ethylacetate, toluene, dichloromethane and chloroform are preferred solvents.

In another aspect, the step to manufacture compound (I) from compound (IVa) or (IVb) can be performed in the absence of a solvent.

In one aspect, the step to manufacture compound (I) from compound (IVa) or (IVb) is performed in the presence of at least one base, which is preferred. This base is different from the base of formula (IVa) or (IVb) when Y=$NR^6$. Particularly suitable are organic cyclic and acyclic aromatic or non-aromatic bases, such as triethylamine, diisopropylamine, pyridine, pyrimidine, trimethylamine, tributylamine, diisopropylethylamine, tert-butyldimethylamine, N-methylpyrrolidine, N-methylpiperidine, N-methylmorpholine, N,N'-dimethylpiperazine, collidine, lutidine or 4-dimethylaminopyridine, and bicyclic amines, such as diazabicycloundecene (DBU) or diazabicyclononene (DBN). Inorganic bases are also suitable as bases to be present in the step to manufacture compound (I) from compound (IVa), for example alkali metal and alkaline earth metal carbonates, such as lithium carbonate or calcium carbonate, alkali metal bicarbonates, such as sodium bicarbonate, alkali metal and alkaline earth metal oxides, such as lithium oxide, sodium oxide, calcium oxide or magnesium oxide, alkali metal and alkaline earth metal hydrides, such as lithium hydride, sodium hydride, potassium hydride or calcium hydride, or alkali metal amides, such as lithium amide, sodium amide or potassium amide. Neutral organic bases, such as DMF or acetamides are particularly suitable as base. The presence of a base in particularly advantageous when Y=$NR^6$ in (IVa) or (IVb).

In one aspect, the step to manufacture compound (I) from compound (IVa) or (IVb) is conducted in the absence of a base. When the reaction is performed in the absence of a base, it is advantageous to work in dilution and with lower temperatures in order to avoid side reactions with HX" which can be formed. Reaction temperatures of from 10 to 40° C., preferably 20-25° C., are preferred when a base is absent.

In a one aspect of the process according to the invention for preparing compounds of the formula (I) from a compound of formula (IVa) or (IVb) is carried out essentially anhydrously.

For the present invention, the term «essentially anhydrous» in intended to denote that a solvent, reagent, reaction mixture and/or additive has a water content of less than 500 ppm and in particular of less than 100 ppm. The water released during the reaction is not taken into account in the stated water content.

The step to manufacture compound (I) from compound (IVa) or (IVb) is often performed at a temperature which generally is equal to or greater than −80° C., preferably equal to or greater than −70° C. and more preferably equal to or greater than −60° C. Often, the temperature is equal to or less than 80° C., preferably equal to or less than 60° C. and more preferably equal to or less than 40° C.

In the step to manufacture compound (I) from compound (IVa) or (IVb), the compound of formula Va, Vb, Vc, Vd or Ve is often used in an amount of equal to or greater than 0.8 mol, preferably equal to or greater than 0.9 mol and more preferably equal to or greater than 0.95 mol based on 1 mol of formula (IVa) or (IVb). Often, the compound of formula (IVa) or (IVb) is used in an amount of equal to or less than 1.2 mol, preferably equal to or less than 1.1 mol and more preferably equal to or less than 1.05 mol based on 1 mol of formula (IVa) or (IVb). Amounts of 3, 5, or more molar equivalents of Va, Vb, Vc, Vd can also be used, such that these compounds are used as solvent. In some cases it has been shown that this can accelerate the reaction. Excess amounts can be recycled into the reaction, e.g. after recovery by extraction and/or distillation.

In the process according to the present invention, the base, when present in the step to manufacture compound (I) from compound (IVa) or (IVb), is often used in an amount of equal to or greater than 0.8 mol, preferably equal to or greater than 0.9 mol and more preferably equal to or greater than 0.95 mol based on 1 mol of formula (IVa) or (IVb). Often, the base is used in an amount of equal to or less than 1.2 mol, preferably equal to or less than 1.1 mol and more preferably equal to or less than 1.05 mol based on 1 mol of formula (IVa) or (IVb). In another aspect, the base can be used in catalytic amounts, based on the compound (I), for example in an amount of from about 0.001 to 0.2 mol per mole of the compound (IVa) or (IVb). However, the base may also be employed in a large excess based on the compound of the formula (IVa) or (IVb), for example as solvent.

It can be advantageous, when X"=F in (Va) or (Vc), to convert X" into Cl in situ during the reaction, by the presence of suitable Cl sources, such as LiCl or $CaCl_2$. This can be the case, for example, when (Va) or (Vc) are difluoroacetylfluoride or trifluoroacetylfluoride. The reaction often is efficient when it is conducted essentially anhydrously.

In the step to manufacture compound (I) from compound (IVa) or (IVb), the reaction can be employed at ambient pressure or, if suitable, at an elevated pressure. This is particularly advantageous if one of the reactants is gaseous at the reaction temperature. Suitable elevated pressures are, for example, from more than 1 bar to 10 bar.

In one aspect, the compound of formula (I) is further used as crude reaction product when manufactured from (IVa) or (IVb), for example in the manufacture of a formula of compound (II). The reaction product may also be separated from any salts produced in the reaction, for example by filtration, washing, decanting or spinnning, and then is reacted further without further purification. When desired, the crude reaction mixture can also be purified, for example by distillation, crystallization, chromatography or distillation.

In one embodiment, the process for the manufacture of a compound of formula (II) from a compound of formula (I)

further comprises the step of manufacturing the compound of formula (IVa) or (IVb), with Y=NR⁶, from a compound of formula (VIa) or (VIb)

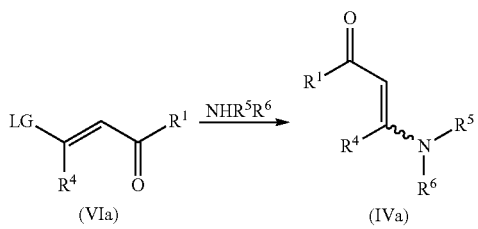

(VIa)    (IVa)

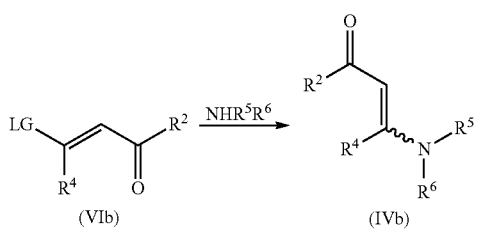

(VIb)    (IVb)

LG is a suitable leaving group, preferably LG is alkoxy R⁷O— or aryloxy ArO—. R⁷ is selected from the group consisting of $C_1$-$C_{12}$-alkyl or $C_3$-$C_{10}$-cycloalkyl group, each of which is optionally substituted by one or more groups selected from the group consisting of —R', —X', —OR', —SR', —NR'₂, —SiR'₃, —COOR', —(C—O)R', —CN and —CONR'₂, where R' is hydrogen or a $C_1$-$C_{12}$-alkyl group and X' is F, Cl, Br, or I. Preferably, R⁷ is methyl, ethyl, n- or i-propyl or i-, n- or tert-butyl, wherein methyl and ethyl are most preferred R⁷. In a particularly preferred aspect, compound (IVb) is manufactured from (VIb), wherein R² is CCl₃ and LG is EtO—. In another particularly preferred aspect, compound (IVb) is manufactured from (VIb), wherein R² is CF₃ and LG is EtO—. The compounds of formula (VIb) and (VIa) are commercially available, such as 4-ethoxy-1,1,1-trifluoro-3-buten-2-one (ETFBO), and their manufacture is known to the person skilled in the art, e.g. from WO2010000871 (ETFBO), which is hereby incorporated by reference for all purposes, or Tietze, L. F. et al, Organic Syntheses, 69, 238-244; 1990 (4-ethoxy-1,1,1-trichloro-3-buten-2-one ETCBO).

R⁵ and R⁶ in the step of manufacturing (IVa) or (IVb) from a compound of formula (VIa) or (VIb) have the same meaning as for the compound of formula (I). In a preferred aspect, R⁵ and R⁶ are Methyl or Ethyl.

In another aspect, the invention concerns the process for the manufacture of an agrochemical or pharmaceutical compound, which comprises the process for the manufacture of the compounds of formula (II), (VII) or (I) mentioned above. In particular, when R¹⁰ is H, often the carboxylic function is activated by formation of the carboxylic acid halide or anhydride, and subsequent reaction with an amine of formula (VI) NR¹²HQ, wherein R¹² is selected from the group consisting of H, $C_1$-$C_{12}$-alkyl, $C_2$-$C_6$ alkenyl or $C_3$-$C_8$-cycloalkyl group, wherein H and C1-C4-alkyl are preferred, to obtain a compound of formula (IX)

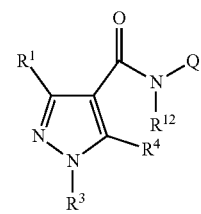

(IX)

wherein Q is an optionally substituted aryl or heteroaryl group. The aryl or heteroaryl group can also be bi- or tricyclic, wherein one or more rings which are bound to the aryl or heteroaryl group can be non-aromatic. Generally, Q is selected from the group consisting of phenyl, naphtalene, 1,2,3,4-tetrahydronaphthalene, 2,3-dihydro-1H-indene, 1,3-dihydroisobenzofuran, 1,3-dihydrobenzo[c]thiophene, 6,7,8,9-tetrahydro-5H-benzo[7]annulene, thiophene, furan, thioazole, thiadiazole, oxazole, oxadiazole, pyridine, pyrimidine, triazine, tetrazine, thiazine, azepine and diazepine, each of which is optionally substituted. In a particular aspect, Q is selected from Q1 to Q38 defined here below:

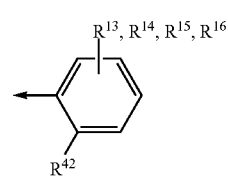

(Q1)

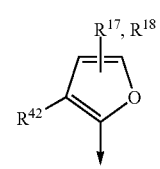

(Q2)

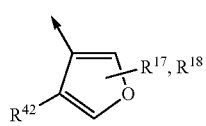

(Q3)

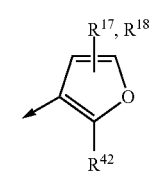

(Q4)

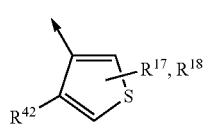

(Q5)

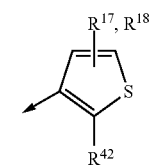

(Q6)

-continued
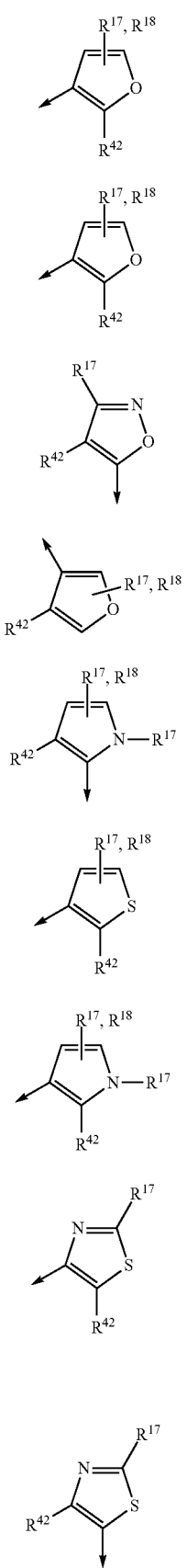
(Q7)
(Q8)
(Q9)
(Q10)
(Q11)
(Q12)
(Q13)
(Q14)
(Q15)
-continued
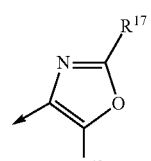
(Q16)
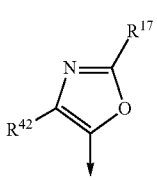
(Q17)
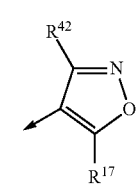
(Q18)
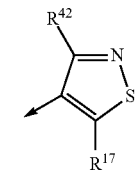
(Q19)
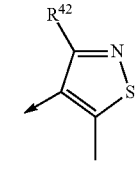
(Q20)
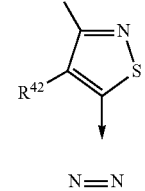
(Q21)
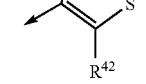
(Q22)
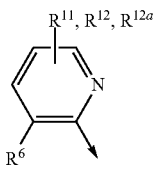
(Q23)
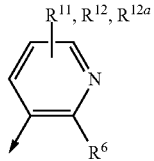
(Q24)

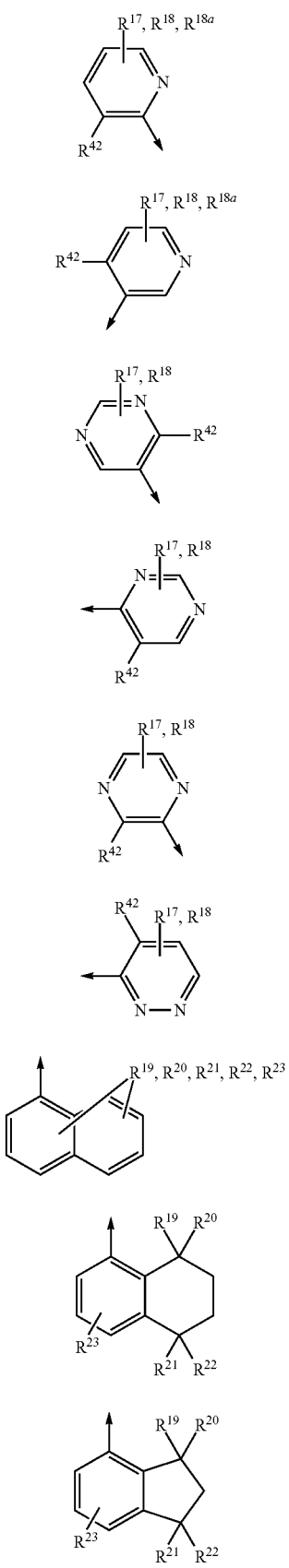

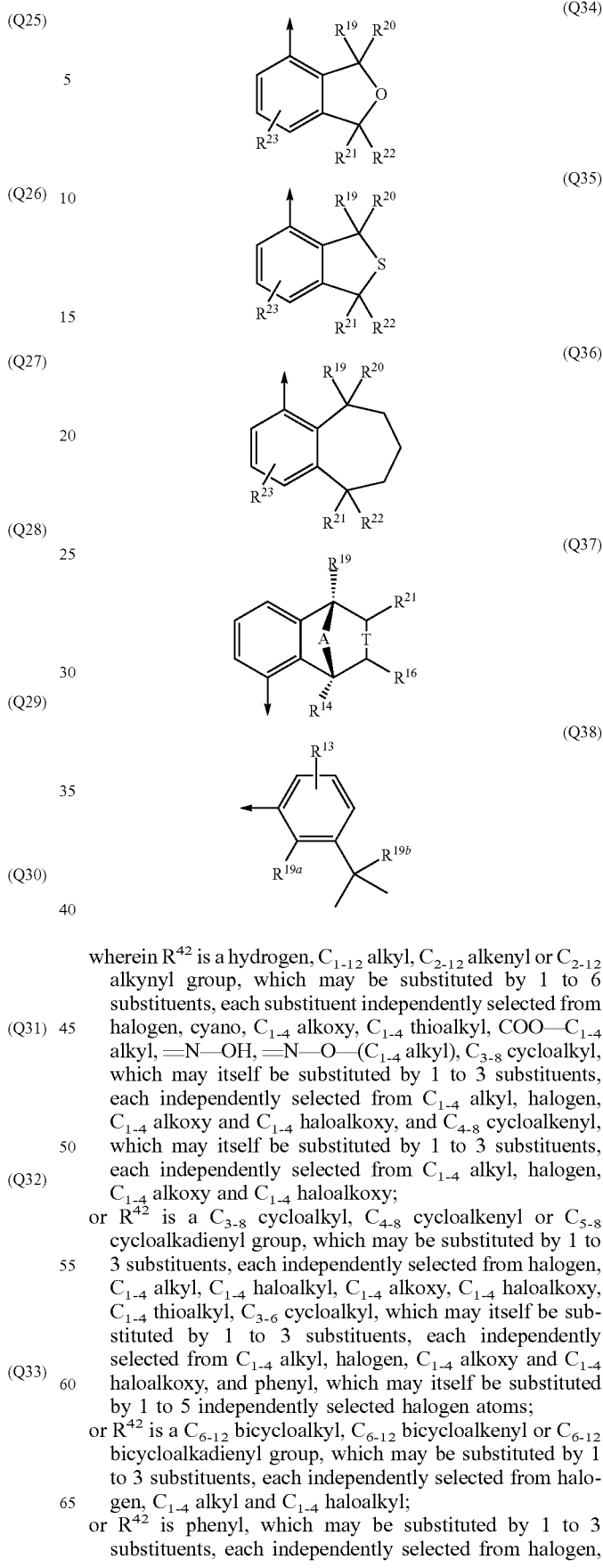

wherein $R^{42}$ is a hydrogen, $C_{1-12}$ alkyl, $C_{2-12}$ alkenyl or $C_{2-12}$ alkynyl group, which may be substituted by 1 to 6 substituents, each substituent independently selected from halogen, cyano, $C_{1-4}$ alkoxy, $C_{1-4}$ thioalkyl, COO—$C_{1-4}$ alkyl, =N—OH, =N—O—($C_{1-4}$ alkyl), $C_{3-8}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and $C_{4-8}$ cycloalkenyl, which may itself be substituted by 1 to 3 substituents, each independently selected from $C_{1-4}$ alkyl, halogen, $C_{1-4}$ alkoxy and $C_{1-4}$ haloalkoxy;

or $R^{42}$ is a $C_{3-8}$ cycloalkyl, $C_{4-8}$ cycloalkenyl or $C_{5-8}$ cycloalkadienyl group, which may be substituted by 1 to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and phenyl, which may itself be substituted by 1 to 5 independently selected halogen atoms;

or $R^{42}$ is a $C_{6-12}$ bicycloalkyl, $C_{6-12}$ bicycloalkenyl or $C_{6-12}$ bicycloalkadienyl group, which may be substituted by 1 to 3 substituents, each independently selected from halogen, $C_{1-4}$ alkyl and $C_{1-4}$ haloalkyl;

or $R^{42}$ is phenyl, which may be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), $(E)_nC\equiv CR$, $(E)_nCR^{34}=CR^{32}R^{33}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl);

or $R^{42}$ is a 5-6 membered heterocyclic ring, wherein the heterocyclic ring contains 1 to 3 heteroatoms, each heteroatom independently chosen from oxygen, sulphur and nitrogen, wherein the heterocyclic ring may be substituted 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$ alkylthio, $C_{1-4}$ haloalkoxy, C(H)=N—O—($C_{1-6}$ alkyl) and C($C_{1-6}$ alkyl)=N—O—($C_{1-6}$ alkyl), $C_{2-5}$ alkenyl, $C_{2-5}$ alkynyl, CHO, COO$C_1$-$C_6$ alkyl, $CrC_4$ alkoxy-$C_1$-$C_4$ alkyl, $CrC_4$ haloalkoxy-$C_1$-$C_4$ alkyl, $(E)_pC\equiv CR$, $(E)_nCR^{34}=CR^{32}R^{33}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and wherein two substituents on adjacent carbon atoms of the 5-6 membered heterocyclic ring together may form a group —$CR^{42a}$—$CR^{42a}$=$CR^{42a}$—$CR^{42a}$—, wherein each $R^{42a}$ independently is selected from hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl);

or $R^{42}$ is an aliphatic saturated or unsaturated group containing 3 to 13 carbon atoms and at least one silicon atom, wherein the aliphatic group may contain 1 to 3 heteroatoms, each heteroatom independently selected from oxygen, nitrogen and sulphur, and wherein the aliphatic group may be substituted by 1 to 4 independently selected halogen atoms;

or $R^{42}$ is $(CR^aR^b)_m$-Cy-$(CR^cR^d)_n$-$A_1$;

or $R^{42}$ is $C_{1-6}$ alkoxy, $C_{1-6}$ haloalkoxy, $C_{2-6}$ alkenyloxy, $C_{2-6}$ haloalkenyloxy, $C_{2-6}$ alkinyloxy, $C_{3-6}$ cycloalkyloxy, $C_{1-4}$ alkyl-$C_{3-7}$ cycloalkyloxy, $C_{5-7}$ cycloalkenyloxy or $C_{1-4}$ alkyl-$C_{5-7}$ cycloalkenyloxy;

E is $C_{1-4}$ alkylene;

p is 0 or 1;

$R^{31}$ is hydrogen, halogen, $C_{1-4}$ alkyl, $C_{1-4}$ haloalkyl, $C_{1-4}$ alkoxy ($C_{1-4}$) alkyl, $C_{1-4}$ haloalkoxy ($C_{1-4}$) alkyl or Si($C_{1-4}$ alkyl)$_3$;

$R^{32}$ and $R^{33}$ are each, independently, hydrogen, halogen, $C_{1-4}$ alkyl or $C_{1-4}$ haloalkyl;

$R^{31}$ is hydrogen, $C_{1-4}$ alkyl or $C_{1-4}$ haloalkyl;

$R^a$, $R^b$, $R^c$ and $R^d$ are each, independently, hydrogen or a $C_{1-4}$ alkyl group, which may substituted by 1 to 6 substituents, each substituent independently selected from halogen, hydroxy, cyano, carboxyl, methoxycarbonyl, ethoxycarbonyl, methoxy, ethoxy, methylsulfonyl, ethylsulfonyl, difluoromethoxy, trifluoromethoxy, trifluoromethylthio and trifluorothiomethoxy;

Cy is a carbocyclic or heterocyclic 3-7 membered ring, which may be saturated, unsaturated or aromatic and which may contain a silicon atom as a ring member, wherein $(CR^aR^b)_m$ and $(CR^cR^d)_n$ may be bound either to the same carbon or silicon atom of Cy or to different atoms separated by 1, 2 or 3 ring members, wherein the carbocyclic or heterocyclic 3-7 membered ring may substituted by 1 to 6 substituents, each substituent independently selected from halogen, $C_{1-4}$ alkyl, $C_{2-4}$ alkenyl, $C_{1-4}$ haloalkyl, $C_{1-4}$ alkoxy and halo-$C_{1-4}$ alkoxy;

$A_1$ is $Si(O_{p1}E^1)(O_qE^2)(O_sE^3)$ and provided that Cy contains a silicon atom as a ring member then $A_1$ may also be hydrogen;

$E^1$ and $E^2$ are independently methyl or ethyl;

$E^3$ is a $C_{1-4}$ alkyl or a $C_{2-4}$ alkenyl group, which may be interrupted by one heteroatom selected from O, S and N, and wherein the $C_{1-4}$ alkyl or $C_{2-4}$ alkenyl group may be substituted by 1 to 3 independently selected halogen atoms;

m and n are each independently 0, 1, 2 or 3;

$p_1$, q and s are each independently 0 or 1;

$R^{13}$, $R^{14}$, $R^{15}$, $R^{16}$, $R^{17}$, $R^{18}$ and $R^{18a}$ are each, independently, hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ thioalkyl or $C_{1-4}$ thiohaloalkyl;

$R^{19}$, $R^{20}$, $R^{21}$, $R^{22}$ and $R^{23}$ are each, independently, hydrogen, halogen, cyano, nitro, $C_{1-4}$ alkyl, $C(O)CH_3$, $C_{1-4}$ haloalkyl, $C_{1-4}$ alkoxy, $C_{1-4}$ haloalkoxy, $C_{1-4}$ thioalkyl, $C_{1-4}$ thiohaloalkyl, hydroxymethyl or $C_{1-4}$ alkoxymethyl;

T is a single or a double bond; and

A is O, $N(R^{24})$, S or $(CR^{25}R^{26})(CR^{27}R^{28})_{m1}(CR^{29}R^{30})_{n1}$;

$R^{24}$ is hydrogen, $C_{1-4}$ alkyl, formyl, $C_{1-4}$ alkoxy($C_{1-4}$)alkyl, C(=O)$C_{1-4}$ alkyl, which may be substituted by halogen or $C_{1-4}$-alkoxy, or C(=O)O—$C_{1-6}$ alkyl, which may be substituted by halogen, $C_{1-4}$ alkoxy or CN;

$R^{25}$, $R^{26}$, $R^{27}$, $R^{28}$, $R^{29}$ and $R^{30}$ are each independently hydrogen, halogen, hydroxy, $C_{1-4}$ alkoxy, $C_{1-6}$ alkyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), $C_{1-6}$ alkenyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), or a 3-7 membered carbocyclic ring, which may contain 1 heteroatom selected from nitrogen and oxygen, and wherein the 3-7 membered carbocyclic ring may be substituted by 1 to 3 methyl groups;

or $R^{25}$, $R^{26}$ together with the carbon atom to which they are attached form a carbonyl-group, a 3-5 membered carbocyclic ring, which may be substituted by 1 to 3 methyl groups, $C_{1-6}$ alkylidene, which may be substituted by 1 to 3 methyl groups, or $C_{3-6}$ cycloalkylidene, which may be substituted by 1 to 3 methyl groups;

$m_1$ is 0 or 1;

$n_1$ is 0 or 1;

$R^{19a}$ is a $C_1$-$C_4$ alkyl, $C_2$-$C_4$ alkenyl or $C_2$-$C_4$ alkynyl group, which may be substituted by 1 to 6 substituents, each substituent independently selected from halogen, hydroxy, cyano, $C_{1-4}$ alkoxycarbonyl, formyl, nitro, $C_1$-$C_4$ alkoxy, $C_1$-$C_4$ haloalkoxy, $C_1$-$C_4$ alkylthio, $C_1$-$C_4$ haloalkylthio, HC(OR$^{35}$)=N— and $R^{36}R^{37}$NN=C(H)—;

$R^{35}$, $R^{36}$ and $R^{37}$ independently of one another are hydrogen or $C_1$-$C_4$ alkyl;

$R^{19b}$ is a $C_1$-$C_6$ alkyl group, which may be substituted by 1 to 6 substituents, each substituent independently selected from halogen, hydroxy, cyano, $C_{1-4}$ alkoxycarbonyl, formyl, nitro, $C_1$-$C_4$ alkoxy, $C_1$-$C_4$ haloalkoxy, $C_1$-$C_4$ alkylthio, $C_1$-$C_4$ haloalkylthio, HC(OR$^{38}$)=N— and $R^{39}R^{40}$NN=C(H)—;

$R^{38}$, $R^{39}$ and $R^{30}$ independently of one another are hydrogen or $C_1$-$C_4$ alkyl;

$R^{19c}$ is hydrogen or halogen; and tautomers/isomers/enantiomers of these compounds.

In a first specific preferred embodiment in relation to a process for the manufacture of compound (IX) which comprises the process for the manufacture of the compound of formula (II), (I) or (VII), Q is a group of formula Q39

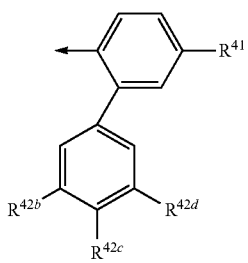
(Q39)

wherein $R^{41}$, $R^{42b}$, $R^{42c}$ and $R^{42d}$ are each, independently, hydrogen or halogen, said halogen is especially chlorine or fluorine.

In a second specific preferred embodiment in relation to a process for the manufacture of compound (IX) which comprises the process for the manufacture of the compound of formula (II), (I) or (VII), Q is a group of formula Q40

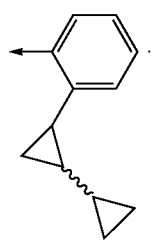
(Q40)

In a third specific preferred embodiment in relation to a process for the manufacture of compound (IX) which comprises the process for the manufacture of the compound of formula (II), (I) or (VII), Q is a group of formula Q41 or Q43

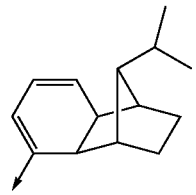
(Q41)

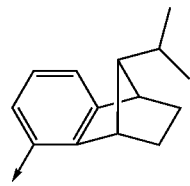
(Q43)

In a fourth specific preferred embodiment in relation to a process for the manufacture of compound (IX) which comprises the process for the manufacture of the compound of formula (II), (I) or (VII), preferably when $R^1$ is $CF_3$, Q is a group of formula Q42

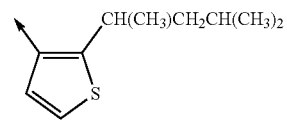
(Q42)

In a fifth specific preferred embodiment in relation to a process for the manufacture of compound (IX) which comprises the process for the manufacture of the compound of formula (II), (I) or (VII), preferably when $R^1$ is $CF_3$, Q is a group of formula A of table W in WO2007009717, in particular group A disclosed in table W in WO2007009717 in connection with compounds W.145 or W.146.

In another process for the manufacture of an agrochemical or pharmaceutical compound, which comprises the process for the manufacture of the compounds of formula (II), when $R^{10}$ is selected from the group consisting of $C_1$-$C_{12}$-alkyl, $C_2$-$C_6$ alkenyl or $C_3$-$C_8$-cycloalkyl group, especially when $R^{10}$ is $C_1$-$C_4$-alkyl, the compound of formula (II) is contacted with an amine of formula (VI) NR$^{12}$HQ, wherein $R^{12}$ is defined as above, wherein Q is defined as above, in the presence of at least one base which is not NR$^{12}$HQ, wherein the at least one base is preferably selected from the group consisting of sterically hindered alcoholates, such as potassium tert-butoxide, sodium tert-butoxide, lithium compounds and silicium compounds. Details of such a procedure are described, for example, in WO2012055864.

In another process for the manufacture of an agrochemical or pharmaceutical compound, which comprises the process for the manufacture of the compounds of formula (II), when $R^{10}$ is selected from the group consisting of $C_1$-$C_{12}$-alkyl, $C_2$-$C_6$ alkenyl or $C_3$-$C_8$-cycloalkyl group, especially when $R^{10}$ is $C_1$-$C_4$-alkyl, is described in WO2012055864, wherein the compound of formula (II) is contacted with an amine of formula (VI) NR$^{12}$HQ, wherein $R^{12}$ is defined as above, wherein Q is defined as above, in the presence of at least one Lewis acid, preferably in the presence of at least one Lewis acid comprising at least one halogen ligand.

In the processes for the manufacture of an agrochemical compound as described above, for example compounds such as N-(3',4'-Dichlor-5-fluorbiphenyl-2-yl)-3-(difluormethyl)-

1-methylpyrazol-4-carboxamid, 3-(difluoromethyl)-1-methyl-N-[2-(3',4',5'-trifluorophenyl)phenyl]pyrazole-4-carboxamide, N-(2-Bicyclopropyl-2-ylphenyl)-3-difluoromethyl-1-methyl-1H-pyrazol-4-carboxylic acid amide, 3-(Difluormethyl)-1-methyl-N-[1,2,3,4-tetrahydro-9-(1-methylethyl)-1,4-methanonaphthalen-5-yl]-1H-pyrazol-4-carboxamid or N-[(1RS,4SR)-9-(dichloromethyl-idene)-1,2,3,4-tetrahydro-1,4-methanonaphthalen-5-yl]-3-(difluoromethyl)-1-methyl-1H-pyrazole-4-carboxamide (and isomers) are obtained.

The invention also relates to compounds of formula (VII)

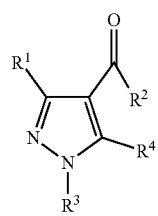
(VII)

in which $R^1$, $R^2$, $R^3$ and $R^4$ are as described above. Examples of (VII) are given in table 2.

TABLE 2

Exemplified compounds of formula (VII)

| | $R^1$ | $R^2$ | $R^3$ | $R^4$ |
|---|---|---|---|---|
| (VII).1 | $CHF_2$ | $CCl_3$ | $CH_3$ | H |
| (VII).2 | $CClF_2$ | $CCl_3$ | $CH_3$ | H |
| (VII).3 | $CF_3$ | $CCl_3$ | $CH_3$ | H |
| (VII).4 | $CHF_2$ | $CF_3$ | $CH_3$ | H |
| (VII).5 | $CClF_2$ | $CF_3$ | $CH_3$ | H |
| (VII).6 | $CCl_3$ | $CF_3$ | $CH_3$ | H |
| (VII).7 | $CHF_2$ | $CBr_3$ | $CH_3$ | H |
| (VII).8 | $CClF_2$ | $CBr_3$ | $CH_3$ | H |
| (VII).9 | $CF_3$ | $CBr_3$ | $CH_3$ | H |

The invention further relates to a process for manufacturing compounds according to formula (VII)

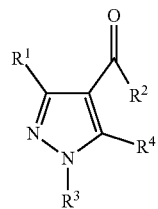
(VII)

which comprises the step of reacting a compound of formula (I) with a compound of formula (III), (VIII) or (V)

$$H_2N—NHR^3 \quad (III)$$

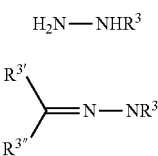
(VIII)

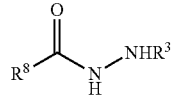
(V)

wherein $R^1$, $R^2$, $R^3$, $R^4$, $R^{3'}$, $R^{3''}$ and $R^8$ are defined as above.

In the process for the manufacture of (VII) comprising the step of reacting a compound of formula (I) with a compound of formula (III), (VIII) or (V) the step of reacting a compound of formula (I) with a compound of formula (III), (VIII) or (V) preferably is conducted in the absence of a base other than (III), (VIII) or (V). With respect to other reaction conditions, such as solvents, temperatures or stoichiometry, the conditions as described for the manufacture of (II) apply. In another aspect, the process for the manufacture of (VII) is carried out essentially anhydrously.

In the reaction of (I) with (VIII), as described before, often, a desired intermediate (XIV) is formed. This reaction is preferably carried out anhydrously.

The invention also relates to a process for the manufacture of a compound of formula (II), which comprises the step of contacting a compound of formula (VII) with a base. The base can be an inorganic or an organic base. Suitable inorganic bases are, for example, alkali metal and alkaline earth metal hydroxides, such as sodium hydroxide, potassium hydroxide or calcium hydroxide, alkali metal and alkaline earth metal oxides, such as lithium oxide, sodium oxide, calcium oxide or magnesium oxide, alkali metal and alkaline earth metal carbonates, such as lithium carbonate or calcium carbonate, alkali metal bicarbonates, such as sodium bicarbonate, alkali metal and alkaline earth metal hydrides, such as lithium hydride, sodium hydride, potassium hydride or calcium hydride, or alkali metal amides, such as lithium amide, sodium amide or potassium amide. Suitable organic bases are, for example primary, secondary or tertiary amines, such as trimethylamine, triethylamine, diisopropylethylamine, tert-butyldimethylamine or ethyldicyclohexylamine, the abovementioned cyclic tertiary amines, such as N-methylpyrrolidine, N-methylpiperidine, N-methylmorpholine, N,N'-dimethylpiperazine, pyridine, collidine, lutidine or 4-dimethylaminopyridine, or bicyclic amines, such as diazabicycloundecene (DBU) or diazabicyclononene (DBN). The invention also relates to a process for the manufacture of a compound of formula (II), which comprises the step of contacting a compound of formula (VII) with a base in the presence of water and/or an alcohol, wherein the compound (II) is defined as above, and the compound of formula (VII) is defined as above. Preferably, the base is an amine, preferably it is trialkylamine, such as triethylamine. In another aspect, the base is an alcoholate, such as, for example, sodium ethanolate. The base can also be an alcoholate of the formula $M^xOR^{10}$ or $M^y(OR^{10})_2$, with $R^{10} \neq H$, which are defined above. The alcohol, when present, can be an alcohol of formula $R^{10}OH$, with $R^{10} \neq H$.

Compound (II) can be present in the form of a carboxylate after the step of contacting a compound of formula (VII) with a base.

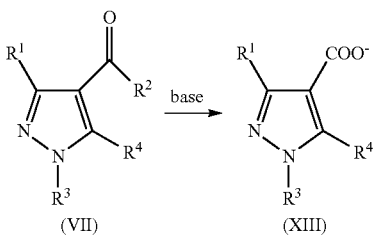

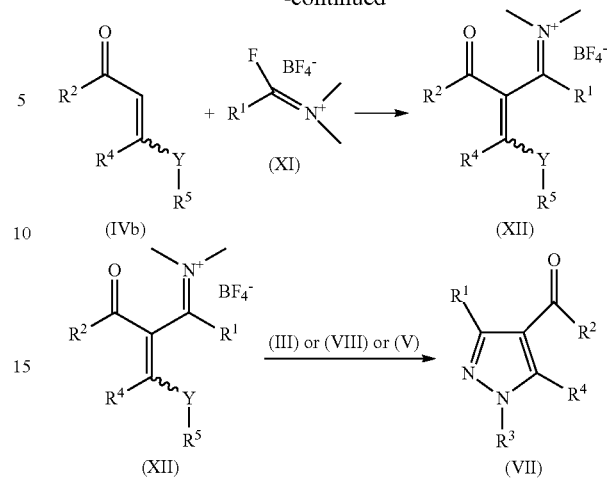

The counterion of the carboxylate (XIII) can preferably be the basic cation B⁻ corresponding to the base present in the step of contacting a compound of formula (VII) with a base, for example the alkali metal and alkaline earth metal cation if alkali metal and alkaline earth metal hydroxides are used as base. In particular, the cation if can be selected from the group $Na^+$, $K^+$, $Li^+$, $Ca^{2+}$, and $Mg^{2+}$, wherein $K^+$ and $Na^+$ are preferred. The cation may also be the cation of an organic base, such as quaternary ammonium cations or cations of formula $NR^{43}{}_3H^+$ wherein each $R^{43}$ independently is H or an organic radical, for example selected from methyl, ethyl, n- or i-propyl or i-, n- or tert-butyl.

The process for manufacturing compound (II) from (VII) can comprise the step of acidification of a reaction mixture comprising carboxylate (XIII) in order to obtain the free carboxylic acid (II) with $R^{10}$=H. The acidification is achieved by addition of suitable acids, in particular aqueous acids, which may be inorganic, such as HCl, $H_2SO_4$, $NaHSO_4$ or $HNO_3$, or organic, such as citric acid. The term "acidification" generally denotes the adjustment of the pH of the reaction mixture by addition of the acid to values of equal to or lower than pH 7, and preferably equal to or less than pH 5. "Acidification" generally denotes the adjustment of the pH value to a value of equal to or greater than 1. For example, a pH value of from 1 to 2 can be suitable.

The compound of formula (VII) can also be obtained by reaction of a compound of formula (XI), which can be obtained by reaction of a compound of formula (X) with $BF_3$, with a compound of formula (IVb), such that a compound of formula (XII) is obtained. (XII) is then reacted with a compound of formula (III), (VIII) or (V), wherein (III) is preferred, to obtain a compound of formula (VII). The compound of formula (X) preferably is 1,1,2,2-Tetrafluoro-N,N-dimethylethylamine or 1,1,2,2,2-pentafluoro-N, N-dimethylethanamine. Y in (XII) preferably is $NR^6$. $R^6$ and $R^5$ are defined as above for compound (I). The generation and further application of iminium salts for fluoroacylations is described, for example, in E. Schmitt et al, Org. Lett., 2015, 17 (18), pp 4510-4513 or WO2008152138. In one aspect, $R^1$ is $CF_2H$, $R^2$ is $CF_3$ or $CCl_3$, wherein $CCl_3$ is preferred and $R^4$ is H. In another aspect, $R^1$ is $CF_3$, $R^2$ is $CF_3$ or $CCl_3$, wherein $CCl_3$ is preferred, and $R^4$ is H. In both aspects, Y is preferably $NR^6$, with $R^6$ and $R^5$=methyl. Also, in both aspects, $R^6$ and $R^5$ can form a ring, such as pyrrolidinyl or piperidinyl. The methyl groups on the nitrogen atom in (X), (XI) or (XII) can also be replaced independently by $C_2-C_8$-alkyl, $C_1-C_8$-haloalkyl, $C_3-C_8$-cycloalkyl, benzyl or phenyl, or together with the nitrogen to which they are attached represent a 3- to 8-membered heterocycle. $BF_3$ can be replaced by another Lewis acid.

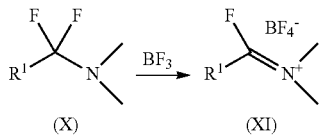

When at least one base is present in the reaction of (XII) with (III), (VIII) or (V), (II), or (II) in the form of (XIII), can be obtained directly.

The invention concerns further compounds of formula (XII), wherein Y, $R^2$, $R^1$, $R^4$ $R^6$ and $R^5$ are defined as above.

In a first preferred embodiment in relation to the compound of formula (XII), Y is O, $R^1$ is $CF_2Cl$, $R^2$ is $CCl_3$, $R^4$ is H and $R^5$ is ethyl.

In a second preferred embodiment in relation to the compound of formula (XII), Y is O, $R^1$ is $CF_2Cl$, $R^2$ is $CF_3$, $R^4$ is H and $R^5$ is ethyl.

In a third preferred embodiment in relation to the compound of formula (XII), Y is O, $R^1$ is $CF_2H$, $R^2$ is $CCl_3$, $R^4$ is H are $R^5$ is ethyl.

In a fourth preferred embodiment in relation to the compound of formula (XII), Y is O, $R^1$ is $CF_2H$, $R^2$ is $CF_3$, $R^4$ is H are $R^5$ is ethyl.

In a fifth preferred embodiment in relation to the compound of formula (XII), Y is O, $R^1$ is $CF_2H$, $R^2$ is $CBr_3$, $R^4$ is H and $R^5$ is ethyl.

In a sixth preferred embodiment in relation to the compound of formula (XII), Y is O, $R^1$ is $CF_2Cl$, $R^2$ is $CF_3$, $R^4$ is H and $R^5$ is ethyl.

In a seventh preferred embodiment in relation to the compound of formula (XII), Y is $NR^6$, $R^1$ is $CF_2Cl$, $R^2$ is $CCl_3$, $R^4$ is H and $R^5$ and $R^6$ are $CH_3$.

In an eighth preferred embodiment in relation to the compound of formula (XII), Y is $NR^6$, $R^1$ is $CF_2Cl$, $R^2$ is $CF_3$, $R^4$ is H and $R^5$ and $R^6$ are $CH_3$.

In a ninth preferred embodiment in relation to the compound of formula (XII), Y is $NR^6$, $R^1$ is $CF_2H$, $R^2$ is $CCl_3$, $R^4$ is H and are $R^5$ and $R^6$ are $CH_3$.

In a tenth preferred embodiment in relation to the compound of formula (XII), Y is $NR^6$, $R^1$ is $CF_2H$, $R^2$ is $CF_3$, $R^4$ is H are $R^5$ and $R^6$ are $CH_3$.

In an eleventh preferred embodiment in relation to the compound of formula (XII), Y is $NR^6$, $R^1$ is $CF_2H$, $R^2$ is $CBr_3$, $R^4$ is H and $R^5$ and $R^6$ are $CH_3$.

In a twelfth preferred embodiment in relation to the compound of formula (XII), Y is $NR^6$, $R^1$ is $CF_2Cl$, $R^2$ is $CF_3$, $R^4$ is H and $R^5$ and $R^6$ are $CH_3$.

In a thirteenth preferred embodiment in relation to the compound of formula (XII), Y is O, $R^1$ is $CF_3$, $R^2$ is $CCl_3$, $R^4$ is H and $R^5$ is ethyl.

In a fourteenth preferred embodiment in relation to the compound of formula (XII), Y is $NR^6$, $R^1$ is $CF_3$, $R^2$ is $CCl_3$, $R^4$ is H and $R^5$ and $R^6$ are $CH_3$.

In a fifteenth preferred embodiment in relation to the compound of formula (XII), one methyl group R⁵ of embodiments seven to twelve is replaced by $C_2$-$C_{12}$-alkyl, $C_3$-$C_{10}$-cycloalkyl, aryl or aralkyl.

In a sixteenth preferred embodiment in relation to the compound of formula (XII), the other methyl group in R⁶ of embodiment thirteen is replaced by $C_2$-$C_{12}$-alkyl, $C_3$-$C_{10}$-cycloalkyl, aryl or aralkyl.

In a seventeenth preferred embodiment in relation to the compound of formula (XII), the ethyl group R⁵ of the first to sixth or thirteenth preferred embodiment in relation to the compound of formula (XII), is replaced by methyl, $C_3$-$C_{12}$-alkyl, $C_3$-$C_{10}$-cycloalkyl, aryl or aralkyl.

In an eighteenth preferred embodiment in relation to the compound of formula (XII), the ethyl group R⁵ of the first to sixth or thirteenth preferred embodiment in relation to the compound of formula (XII), is replaced by methyl, $C_3$-$C_{12}$-alkyl, $C_3$-$C_{10}$-cycloalkyl, aryl or aralkyl.

In a nineteenth preferred embodiment in relation to the compound of formula (XII), R⁵ and R⁶ of the seventh to seventeenth preferred embodiment in relation to the compound of formula (XII), together with the nitrogen atom to which the two radicals are attached, are an optionally substituted 5- to 10-membered heterocyclic radical which, in addition to the nitrogen atom, can contain a further 1, 2 or 3 heteroatoms selected from the group consisting of O, N and S as ring members.

The invention also concerns the use of a compound of formula (XII) for the manufacture of a compound of formula (II), (VII) or (XIII).

The invention further concerns a process for the manufacture of a compound of formula (II), (VII) or (XIII), which comprises the step of reacting a compound of formula (XII) with a compound of formula (III), (VIII) or (V), which is optionally performed in the presence of a base, and which optionally comprises a step of acidification of a reaction mixture comprising a compound of formula (XIII).

The invention also concerns a process for the manufacture of an agrochemical or pharmaceutical compound, which comprises the use of the compound for the manufacture of a compound of formula (II), (VII) or (XIII), or which comprises the process for the manufacture of a compound of formula (II), (VII) or (XIII), which comprises the step of reacting a compound of formula (XII) with a compound of formula (III), (VIII) or (V), which is optionally performed in the presence of a base, and which optionally comprises a step of acidification of a reaction mixture comprising a compound of formula (XIII).

In one embodiment, the invention concerns the process for the manufacture of an agrochemical or pharmaceutical compound, wherein the compound (VII) is reacted with at least one amine of formula (VI) $NR^{12}HQ$, wherein $R^{12}$ is selected from the group consisting of H, $C_1$-$C_{12}$-alkyl, $C_2$-$C_6$ alkenyl or $C_3$-$C_8$-cycloalkyl group, wherein H and $C_1$-$C_4$-alkyl are preferred, wherein Q is defined as above. In one preferred embodiment, R² in (VII) is $CCl_3$, R¹ is $CF_2H$, $CClF_2$ or $CF_3$, wherein $CF_2H$ is preferred, R⁴ is H and R³ is methyl. In one preferred embodiment, R² in (VII) is $CF_3$, R¹ is $CF_2H$, $CClF_2$ or $CF_3$, wherein $CF_2H$ and CF3 are preferred, R⁴ is H and R³ is methyl. In one aspect, the process further comprises process for manufacturing a compound according to formula (VII) as described above. In a specific embodiment, the invention concerns the process for the manufacture of an agrochemical or pharmaceutical compound, wherein (VII) is reacted with an amine of formula (VI) $NR^{12}HQ$, wherein $R^{12}$ is selected from the group consisting of H, $C_1$-$C_{12}$-alkyl, $C_2$-$C_6$ alkenyl or $C_3$-$C_8$- cycloalkyl group, wherein H and $C_1$-$C_4$-alkyl are preferred, to obtain a compound of formula (IX)

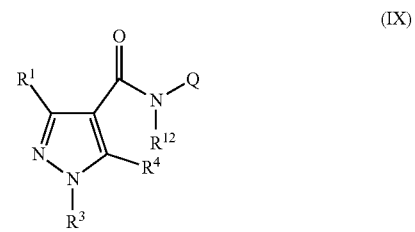

(IX)

Preferably, in the process described above, at least one additional base which is not (VI) is present in the reaction. Preferably, the at least additional one base, which is not (IV), which is present in the reaction between (VI) and (VII) is a non-nucleophilic base. The at least one additional non-nucleophilic base can be an organic or inorganic base. Non-nucleophilic organic bases which are suitable are, for example, N,N-diisopropylethylamine, 1,8-diazabicycloundec-7-ene (DBU), 2,6-Di-tert-butylpyridine, phosphazene bases, such as t-Bu-$P_4$, 1,1,3,3-tetramethylguanidine (TMG), N,N,N',N'',N''-pentamethyldiethylenetriamine (PMDTA), 1,1,4,7,10,10-hexamethyltriethylenetetraamine; N,N,N',N'tetramethylethylenediamine (TMEDA); N,N,N', N'-tetraethylethylenediamine (TEEDA), generally tertiary amines, such as triethylamine, or sterically hindered sec. amines, such as diisopropylamine or N,N-diisopropylethylamine. Of the organic non-nucleophilic bases, TMG, triethylamine, PMDTA and diisopropylamine are preferred. Most preferred is TMG. Non-nucleophilic inorganic bases which are suitable are, for example, potassium or sodium tert-butoxide, sodium or potassium bis(trimethylsilyl)amide, lithium tetramethylpiperidide, sodium hydride and potassium hydride. The at least one, preferably non-nucleophilic, additional base present in the reaction usually is present in a cumulative substoichiometric, related to compound (VII), amount. "Cumulative" intends to represent the sum of all non-nucleophilic, additional bases present in the reaction. Often, the at least one, preferably non-nucleophilic, additional base present in the reaction is present in a cumulative, related to compound (VII), amount of equal to or more than 1 mol %, preferably equal to or more than 5 mol %, more preferably equal to or more than 10 mol %. Amounts of equal to or more than 20 mol % or even 30 mol % are suitable as well. Generally, the at least one, preferably non-nucleophilic, additional base present in the reaction is present in a cumulative, related to compound (VII), amount of less than 100 mol %, preferably equal to or less than 50 mol %, more preferably equal to or more less 40 mol %. In another aspect, the at least one, preferably non-nucleophilic, additional base present in the reaction can also be employed in a cumulative amount which is equal to or more than the amount of (VII) present in the reaction. The at least one additional base can, for example, be present in a two- or three-fold molar excess. The at least one additional base can act as solvent.

The process for the manufacture of an agrochemical or pharmaceutical compound, wherein the compound (VII) is reacted with an amine of formula (VI) often is performed in the presence of at least one solvent. The at least one solvent advantageously is a non-nucleophilic, aprotic solvent. Suitable solvents are, for example, optionally substituted aromatic hydrocarbons, such as for example xylene, benzene or toluene, optionally substituted aliphatic hydrocarbons, such as hexane or halocarbons such as chloroform, ethers such as diethylether or THF, hexamethylphosphoramid (HMPT), dimethyl sulfoxide (DMSO) or dimethylformamide (DMF). Preferably, the at least one solvent is toluene. Preferably, the reaction is carried out in a ratio of solvent: (VII) of from 90:10 to 20:80. Preferably, the ratio of solvent/(VII) is from 40:60 to 60:40. The process for the manufacture of an agrochemical or pharmaceutical compound, wherein the compound (VII) is reacted with an amine of formula (VI) often is performed at a temperature of from −40° C. to 110° C. Generally, the reaction is carried out at a temperature of equal to or more than −40° C., preferably equal to or more than −30° C., and more preferably of more than −20° C. Often, the reaction is carried out at a temperature of equal to or less than 110°, preferably equal to or less than 90° C. and more preferably equal to or less than −70° C. In one aspect, the reactants are contacted first at a first temperature within the given interval, and are reacted after completed addition of the reactants, optionally after a certain time at the first reaction temperature, at a second temperature within the given temperature interval. The reaction time after completed addition of the reactants generally is from 10 minutes to 48 hours. Often, the reaction time after completed addition of the reactants is equal to or more than 10 minutes, preferably equal to or more than 30 minutes, and more preferably or more than 1 hour. Often, the reaction time after completed addition of the reactants is equal to or less than 48 hours, preferably equal to or less than 24 hours, and more preferably or less than 12 hour. In some cases, a reaction time of 3 hours is advantageous. Generally, the reaction mixture is worked up by removal of the volatiles, for example under vacuum and/or heat, which often is followed by addition of water or an aqueous phase. The addition of aliphatic or aromatic hydrocarbons, such as hexane, can also be advantageous. The often solid product can be triturated with water and/or an aliphatic hydrocarbon such as hexane. In the process for the manufacture of an agrochemical or pharmaceutical compound, wherein the compound (VII) is reacted with an amine of formula (VI), the amine of formula (VI) often is used in slight stoichiometric excess. Often, the amine of formula (VI) is present in an amount of equal to or more than 1.05 molar equivalents, based on amount (VII), preferably equal to or more than 1.1 molar equivalents and more preferably equal to or more than 1.1 molar equivalents. Generally, the amine of formula (VI) is present in an amount of equal to or less than 2 molar equivalents, based on amount (VII), preferably equal to or less than 1.9 molar equivalents and more preferably equal to or less than 1.8 molar equivalents.

In such a process for the manufacture of an agrochemical compound, for example compounds such as N-(3',4'-Dichlor-5-fluorbiphenyl-2-yl)-3-(difluormethyl)-1-methylpyrazol-4-carboxamid, 3-(difluoromethyl)-1-methyl-N-[2-(3',4',5'-trifluorophenyl)phenyl]pyrazole-4-carboxamide, N-(2-Bicyclopropyl-2-ylphenyl)-3-difluoromethyl-1-methyl-1H-pyrazol-4-carboxylic acid amide, 3-(Difluormethyl)-1-methyl-N-[1,2,3,4-tetrahydro-9-(1-methylethyl)-1,4-methanonaphthalen-5-yl]-1H-pyrazol-4-carboxamid, N-[2-(1,3-Dimethylbutyl)thien-3-yl]-1-methyl-3-trifluormethyl-1H-pyrazol-4-carboxamid (Penthiopyrad) or N-[(1RS, 4SR)-9-(dichloromethyliden)-1,2,3,4-tetrahydro-1,4-methanonaphthalen-5-yl]-3-(difluoromethyl)-1-methyl-1H-pyrazole-4-carboxamide (and isomers) are obtained.

In one embodiment of the present invention, two or more compounds of formula (VI) are reacted with the compound of formula (VII) to obtain a mixture of at least two compounds of formula (IX). The ratio of at least two or more compounds of formula (VI) depends on the intended ratio of compounds (IX), and may be, for example, 10:90, 20:80, 30:70, 40:60, 50:50, 60:40, 70:30, 80:20 or 90:10.

The new compounds and processes according to the present invention allow for efficient syntheses of agrochemical and pharmaceutical compounds. The present processes for obtaining agrochemically or pharmaceutically active ingredients or intermediates thereof generally comprise less steps than currently available processes, allowing for economically and ecologically advantageous manufacture. Often, the process steps display good to excellent yields and selectivities. Waste can often be reduced.

Should the disclosure of any patents, patent applications, and publications which are incorporated herein by reference conflict with the description of the present application to the extent that it may render a term unclear, the present description shall take precedence.

The following examples are intended to further explain the invention without limiting it.

EXAMPLES 4-ethoxy-1,1,1-trifluorobut-3-en-2-one (ETFBO) is obtained by the process described in EP1644306B1, Example 2. 4-ethoxy-1,1,1-trichlorobut-3-en-2-one (ETCBO) is obtained in the same manner by exchanging trifluoroacetylchloride by trichloroacetylchloride. Difluoroacetylfluoride (DFAF) and chlorodifluoroacetylchloride (CDAC) can be obtained from commercial sources, or manufactured according to the publications cited in the description. 3',4'-dichloro-5-fluorobiphenyl-2-amine, 3',4', 5'-trifluorobiphenyl-2-amine and 2-(bi(cyclopropan)-2-yl) aniline can be obtained from commercial sources.

Example 1

4-(dimethylamino)-1,1,1-trifluorobut-3-en-2-one

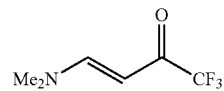

4-ethoxy-1,1,1-trifluorobut-3-en-2-one (ETFBO, 20 g, 0.12 mol) is mixed with 120 mL of dichloromethane and cooled to −5° C. 40% v/v of aqueous dimethylamine (1.1 eq) is added, the mixture is stirred for 10 minutes at −5° C., warmed to room temperature by removing the ice bath and stirred for one hour at room temperature. The mixture is washed with brine, dried over $NaSO_4$ and the volatiles are removed in vacuo. The product is used without further purification, or can also be recrystallized from cold $Et_2O$/hexanes (1:50).

Example 2

3-((dimethylamino)methylene)-1,1,1,5,5-pentafluoropentane-2,4-dione

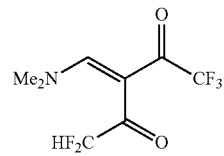

20 g of the product of example 1 is mixed with 140 mL dichloromethane. Pyridine (1.05 eq) is added and the mixture is cooled to −15° C. Difluoroacetylfluoride (DFAF, 1.05 eq) is introduced over a period of 60 minutes. The mixture is stirred at −15° C. for 20 minutes, slowly warmed to room temperature and then heated to 50° C. for 24 hours. The mixture cooled to 20° C., diluted with water (80 mL), mixed thoroughly, the phases are separated and the aqueous phase extracted twice with dichloromethane. The combined extracts are concentrated in vacuo to remove the volatiles.

Example 3

3-(difluoromethyl)-1-methyl-1H-pyrazole-4-carboxylic acid

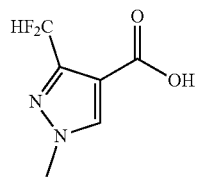

Monomethylhydrazine (40% v/v in water, 1.05 eq), 15 g of the product of example 2 and 2N aqueous KOH (1.1 eq) are mixed with 80 mL acetonitrile. The mixture is stirred at room temperature for 14 hours. The mixture is then heated to 80° C. for 30 minutes, cooled to room temperature and the volatiles are removed in vacuo. The organic phase is washed twice with ethyl acetate, and the organic phase discarded. The aqueous phase is acidified with 2N HCl, the resulting suspension is filtered and the solids washed with cold water to yield the product.

Example 4

1-chloro-3-(ethoxymethylene)-1,1,5,5,5-pentafluoro-pentane-2,4-dione

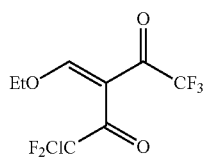

20 g of ETFBO is mixed with 140 mL dichloromethane. Pyridine (1.05 eq) is added and the mixture is cooled to −15° C. Chlorodifluoroacetylchloride (CDAC, 1.05 eq) in dichloromethane is added over a period of 60 minutes. The mixture is stirred at −15° C. for 20 minutes, slowly warmed to room temperature and then heated to 50° C. for 24 hours. The mixture cooled to 20° C., diluted with water (80 mL), mixed thoroughly, the phases are separated and the aqueous phase extracted twice with dichloromethane. The combined extracts are dried over $Na_2SO_4$ and concentrated in vacuo to remove the volatiles.

Alternatively, the reaction mixture is not submitted to an aqueous extraction step but, optionally after incomplete or complete concentration, used directly in a cyclization reaction such as example 5.

Example 5

1-(3-(chlorodifluoromethyl)-1-methyl-1H-pyrazol-4-yl)-2,2,2-trifluoroethanone

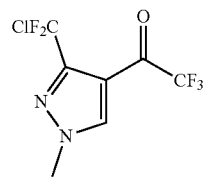

Monomethylhydrazine (40% v/v in water, 1.05 eq) and 15 g in appr. 20 mL dichloromethane of the product of example 4 are diluted with 80 mL acetonitrile. The dichloromethane is removed in vacuo. The mixture is stirred at room temperature for 14 hours. The volatiles are removed in vacuo. The mixture is diluted with tetrahydrofurane, the THF phase is washed with brine. The organic phase is dried over $NaSO_4$ and volatiles removed in vacuo.

Example 6

1,1,1-trichloro-3-(ethoxymethylene)-5,5-difluoro-pentane-2,4-dione

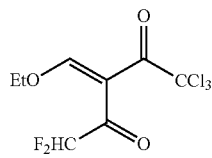

20 g of ETCBO is dissolved in 40 mL pyridine, and the mixture is cooled to −15° C. Difluoroacetylfluoride (DFAF, 2 eq) is introduced over a period of 60 minutes. The mixture is stirred at −15° C. for 20 minutes, slowly warmed to room temperature, then heated to 50° C. and stirred at 50° C. for another 24 hours. The reaction product is used, optionally after incomplete or complete concentration, as a crude product in example 7.

Example 7

2,2,2-trichloro-1-(3-(difluoromethyl)-1-methyl-1H-pyrazol-4-yl)ethanone

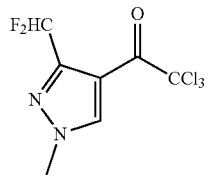

Monomethylhydrazine (MMH, 40% v/v in water, 1.05 eq) is cooled to 20° C. and 15 g of the crude product of example 6 in approximately 45 mL of dichloromethane are added to the MMH. After 1 hour, the mixture is slowly warmed to room temperature and diluted with 20 mL water. The mixture is acidified with 1N HCl, the organic phase is separated, dried over Na$_2$SO$_4$ and the volatiles are removed in vacuo. The crude product is purified by column chromatography (dichloromethane:hexanes 2:3).

Example 8

3-(difluoromethyl)-1-methyl-1H-pyrazole-4-carboxylic acid

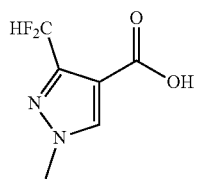

Monomethylhydrazine (40% v/v in water, 1.05 eq), 15 g of the product of example 7 and 2N aqueous KOH (1.1 eq) are mixed with 80 mL acetonitrile. The mixture is stirred at room temperature for 14 hours. The mixture is then heated to 80° C. for 30 minutes, cooled to room temperature and the volatiles are removed in vacuo. The organic phase is washed twice with ethyl acetate, and the organic phase discarded. The aqueous phase is acidified with 2N HCl, the resulting suspension is filtered and the solids washed with cold water to yield the product.

Example 9

Bixafen (N-(3',4'-dichloro-5-fluorobiphenyl-2-yl)-3-(difluoromethyl)-1-methyl-1H-pyrazole-4-carboxamide)

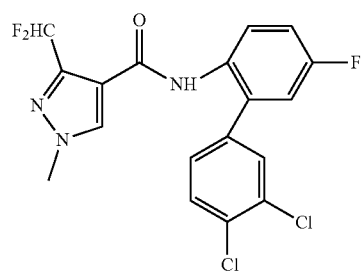 [SMILES: Cn1cc(C(=O)Nc2ccc(F)cc2-c2ccc(Cl)c(Cl)c2)c(C(F)F)n1]

The product of example 7 (5.0 g, 18 mmol) and 3',4'-dichloro-5-fluorobiphenyl-2-amine (4.6 g, 18 mmol) are dissolved in 30 ml dry toluene. To this solution 1,1,3,3-tetramethylguanidine (TMG, 0.2 eq) is added and the mixture is stirred at room temperature for 16 hours. The volatiles of the resulting yellow suspension are evaporated and the residue is triturated with cold water to yield a gray suspension. Solids are filtered, washed with water and dried yielding crude Bixafen.

Example 10

Fluxapyroxad (3-(difluoromethyl)-1-methyl-N-(3',4',5'-trifluorobiphenyl-2-yl)-1H-pyrazole-4-carboxamide)

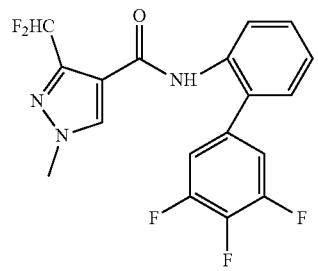 [SMILES: Cn1cc(C(=O)Nc2ccccc2-c2cc(F)c(F)c(F)c2)c(C(F)F)n1]

Fluxapyroxad is obtained using the procedure of example 9, wherein 3',4',5'-trifluorobiphenyl-2-amine is used instead of 3',4'-dichloro-5-fluorobiphenyl-2-amine.

Example 11

Sedaxane (N-(2-(bi(cyclopropan)-2-yl)phenyl)-3-(difluoromethyl)-1-methyl-1H-pyrazole-4-carboxamide)

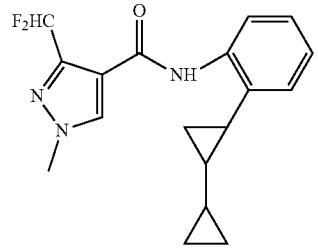 [SMILES: Cn1cc(C(=O)Nc2ccccc2C2CC2C2CC2)c(C(F)F)n1]

Sedaxane is obtained using the procedure of example 9, wherein 2-(bi(cyclopropan)-2-yl)aniline is used instead of 3',4'-dichloro-5-fluorobiphenyl-2-amine.

Example 12

1,1,1-trichloro-3-(ethoxymethylene)-5,5,5-trifluoropentane-2,4-dione

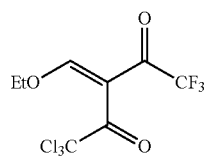

20 g of ETCBO is mixed with 40 mL pyridine in a hastelloy reactor. The reactor is sealed and trifluoroacetylchloride (TFAC, 2 eq) is introduced over a period of 60 minutes. The mixture is brought to a temperature of 50° C. and stirred for 16 hours. The reaction product is used, optionally after incomplete or complete concentration, as a crude product in example 13.

Example 13

2,2,2-trichloro-1-(1-methyl-3-(trifluoromethyl)-1H-pyrazol-4-yl)ethanone

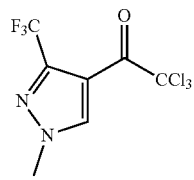

Monomethylhydrazine (40% v/v in water, 1.05 eq) and 15 g of the product of example 12 mixed with 80 mL acetonitrile at room temperature. The mixture is stirred at room temperature for 14 hours. The volatiles are removed in vacuo to yield the crude reaction product.

Example 14

1-methyl-3-(trifluoromethyl)-1H-pyrazole-4-carboxylic acid

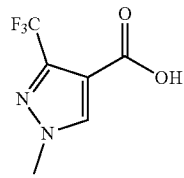

1-methyl-3-(trifluoromethyl)-1H-pyrazole-4-carboxylic acid is obtained using the procedure of example 8, wherein the product of example 13 is used instead of the product of example 7.

Example 15

3-(difluoromethyl)-1-methyl-1H-pyrazole-4-carboxylic acid

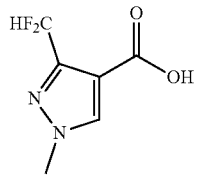

0.231 mol 1,1,1-trichloro-4-(dimethylamino)-but-3-en-2-one, obtained by reaction between 1,1,1-trichloro-4-ethoxybut-3-en-2-one and dimethylamine, were reacted with 0.46 mol difluoroacetylchloride in dimethylformamide and ethylacetate in the presence of $Na_2CO_3$ to obtain, after aqueous workup, drying of combined organic phases and evaporation of volatiles, 1,1,1-trichloro-3-((dimethylamino)methylene)-5,5-difluoropentane-2,4-dione as yellow crystals. 0.178 mol (1 eq) of 1,1,1-trichloro-3-((dimethylamino)methylene)-5,5-difluoropentane-2,4-dione were suspended in ethanol and reacted with 1 eq 1-benzylidene-2-methylhydrazine in the presence of 1 eq NaHSO4 at room temperature for 8 hours. The resulting suspension was quenched in water, the resulting suspension filtered, washed with water, and dried to obtain (3-(2-benzylidene-1-methylhydrazinyl)methylene)-1,1,1-trichloro-5,5-difluoropentane-2,4-dione as light yellow solid. 0.162 mol of (3-(2-benzylidene-1-methylhydrazinyl)methylene)-1,1,1-trichloro-5,5-difluoropentane-2,4-dione was suspended in dimethoxyethane and 63 mL 2.5M aq. HCl were added. The mixture was stirred for 20 hours at room temperature, then diluted in ethylacetate. The combined organic phases were washed with water, brine, dried over $Na_2SO_4$ and evaporated to yield 2,2,2-trichloro-1-(3-(difluoromethyl)-1-methyl-1H-pyrazol-4-yl)ethanone as yellow liquid. 0.1497 (1 eq) 2,2,2-trichloro-1-(3-(difluoromethyl)-1-methyl-1H-pyrazol-4-yl)ethanone were diluted in toluene and 1.1 eq NaOH as 10% aq. solution were added. The mixture was stirred at room temperature overnight. The toluene phase was separated, aqueous phase extracted with toluene and combined organic phases discarded. The aqueous phase was cooled in ice and about 18 mL 32% HCl added under vigorous stirring to reach a pH of 1-2. The resulting suspension was filtered, washed with cold water and dried in vacuum. 3-(difluoromethyl)-1-methyl-1H-pyrazole-4-carboxylic acid was obtained in +99% purity as solid and contained no regioisomer. The combined yield, starting from 1,1,1-trichloro-3-((dimethylamino)methylene)-5,5-difluoropentane-2,4-dione, over three steps was 77%.

Example 16

2,2,2-trichloro-1-(3-(difluoromethyl)-1-methyl-1H-pyrazol-4-yl)ethanone

Under nitrogen, 17.73 g (49.49 mmol) of a 19% solution of $BF_3$ in acetonitrile are cooled to 0° C. and 7.38 g (50.22 mmol) of 1,1,2,2-tetrafluoro-N,N-dimethylethanamine (TFEDMA) are added. The mixture is slowly warmed to 23° C., stirred for 2 hours at this temperature, and cooled to 0° C. A solution of 10.74 g (50 mmol) 1,1,1-trichloro-4-(dimethylamino)-but-3-en-2-one, obtained by reaction between 1,1,1-trichloro-4-ethoxybut-3-en-2-one and dimethylamine, in 10 mL anh. acetonitrile are slowly added. The mixture is slowly warmed to 23° C. and stirred for 2 hours at this temperature. The intermediary product vinamidinium salt can be used without further purification. The solution is cooled on ice, and 2.73 g (59.33 mmol) of methyl hydrazine in acetonitrile are added. The mixture is warmed to 23° C. and stirred at this temperature for 48 hours. The mixture is quenched with sat. NaHCO3 solution, phases separated and aq. phase extracted twice with ethyl acetate. Combined organic phases are washed with brine, dried over $Na_2SO_4$ and solvents removed. The product 2,2,2-trichloro-1-(3-(difluoromethyl)-1-methyl-1H-pyrazol-4-yl)ethanone is obtained as a crude product.

The invention claimed is:

1. A compound according to formula (I) or formula (XII)

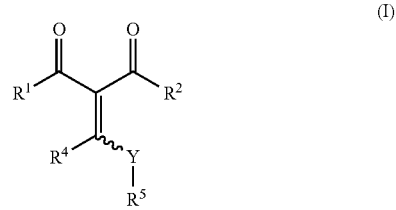

(XII)

wherein
R¹ is selected from the group consisting of $CF_2Cl$, $CF_2H$, $CFCl_2$, $CFClH$, $CF_2Br$, $CCl_3$, $CF_3$, $CBr_3$, and $CI_3$;
R² is $CHal_3$ wherein Hal is a halogen and each Hal is selected independently;
wherein, when R² is $CF_3$, R¹ contains two, one or zero fluorine atoms or,
when R² is $CCl_3$, R¹ contains two, one or zero chlorine atoms,
Y is selected from the group consisting of S, O and $NR^6$,
R⁴ is selected from the group consisting of H, X', COOR', OR', SR', C(O)NR'₂, wherein R' are selected independently in C(O)NR'₂ where R' is hydrogen or a $C_1$-$C_{12}$-alkyl group, CN, $C_1$-$C_{12}$-alkyl, $C_2$-$C_6$ alkenyl, aryl, cycloalkyl, aralkyl, heteroaryl, each of which is optionally substituted, and X' is F, Cl, Br, or I;
R⁵ and R⁶ independently are selected from the group consisting of $C_1$-$C_{12}$-alkyl, $C_2$-$C_6$ alkenyl or $C_3$-$C_{10}$-cycloalkyl group, each of which is optionally substituted
or, when Y=$NR^6$, R⁵ together with R⁶ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members.

2. The compound according to claim 1, wherein R² is selected from the group consisting of $CCl_3$, $CF_3$, $CBr_3$, and $CI_3$.

3. The compound according to claim 1, wherein
R¹ is $CF_2Cl$, Y is O, R² is $CCl_3$, R⁴ is H, R⁵ is ethyl or
R¹ is $CF_2Cl$, Y is O, R² is $CF_3$, R⁴ is H, R⁵ is ethyl or
R¹ is $CF_2H$, Y is O, R² is $CCl_3$, R⁴ is H, R⁵ is ethyl or
R¹ is $CF_2H$, Y is O, R² is $CF_3$, R⁴ is H, R⁵ is ethyl or
R¹ is $CF_2H$, Y is O, R² is $CBr_3$, R⁴ is H, R⁵ is ethyl or
R¹ is $CF_2Cl$, Y is O, R² is $CF_3$, R⁴ is H, R⁵ is ethyl, or
R¹ is $CF_2Cl$, Y is $NR^6$, R² is $CCl_3$, R⁴ is H, R⁵ and R⁶ are $CH_3$ or
R¹ is $CF_2Cl$, Y is $NR^6$, R² is $CF_3$, R⁴ is H, R⁵ and R⁶ are $CH_3$ or
R¹ is $CF_2H$, Y is $NR^6$, R² is $CCl_3$, R⁴ is H, R⁵ and R⁶ are $CH_3$ or
R¹ is $CF_2H$, Y is $NR^6$, R² is $CF_3$, R⁴ is H, R⁵ and R⁶ are $CH_3$ or
R¹ is $CF_2H$, Y is $NR^6$, R² is $CBr_3$, R⁴ is H, R⁵ and R⁶ are $CH_3$ or
R¹ is $CF_3$, Y is O, R² is $CCl_3$, R⁴ is H, R⁵ is ethyl, or
R¹ is $CF_3$, Y is $NR^6$, R² is $CCl_3$, R⁴ is H, R⁵ and R⁶ are $CH_3$ or
R¹ is $CF_2Cl$, Y is $NR^6$, R² is $CF_3$, R⁴ is H, R⁵ and R⁶ are $CH_3$.

4. A process for manufacturing a compound according to formula (II)

(II)

the process comprising the step of reacting a compound of formula (I) according to claim 1 with a compound of formula (III), (VIII) or (V)

$H_2N$—$NHR^3$ (III)

(VIII)

(V)

wherein R³ in (III) and (V) is, or R³, R³' and R³'' independently from each other in (VIII) are, selected from the group consisting of $C_1$-$C_{12}$-alkyl, $C_2$-$C_6$ alkenyl, cycloalkyl, aryl, heteroaryl, aralkyl, and for R³' and R³'' H, each of which is optionally substituted, R¹⁰ is selected from the group consisting of H, $C_1$-$C_{12}$-alkyl, $C_2$-$C_6$ alkenyl or $C_3$-$C_8$-cycloalkyl group, each of which is optionally substituted, R⁸ is selected from the group consisting of R⁹=$C_1$-$C_{12}$-alkyl, $OR^9$ and $NR^{11}R^{11'}$, N,N-diisopropylethylamine wherein $R^{11}$ and $R^{11'}$ independently are selected from the group consisting of $C_1$-$C_{12}$-alkyl and H.

5. The process according to claim 4, wherein the process is performed in the presence of at least one base.

6. A process for manufacturing a compound according to formula (VII)

(VII)

the process comprising the step of reacting a compound of formula (I) according to claim 1 with a compound of formula (III), (VIII) or (V)

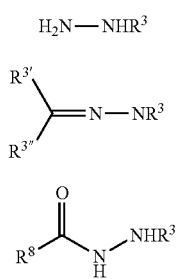

(III)

(VIII)

(V)

wherein R³ in (III) and (V) is, or R³, R³' and R³''' independently from each other in (VIII) are, selected from the group consisting of $C_1$-$C_{12}$-alkyl, $C_2$-$C_6$ alkenyl, cycloalkyl, aryl, heteroaryl, aralkyl, and for R³' and R³'' H, each of which is optionally substituted, $R^{10}$ is selected from the group consisting of H, $C_1$-$C_{12}$-alkyl, $C_2$-$C_6$ alkenyl or $C_3$-$C_8$-cycloalkyl group, each of which is optionally substituted, $R^8$ is selected from the group consisting of $R^9$=$C_1$-$C_{12}$-alkyl, $OR^9$ and $NR^{11}R^{11'}$, wherein $R^{11}$ and $R^{11'}$ independently are selected from the group consisting of $C_1$-$C_{12}$-alkyl and H.

7. A process for the manufacture of a compound of formula (II),

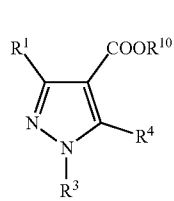

(II)

wherein $R^{10}$ is selected from the group consisting of H, $C_1$-$C_{12}$-alkyl, $C_2$-$C_6$ alkenyl or $C_3$-$C_8$-cycloalkyl group, each of which is optionally substituted, the process comprising the step of contacting a compound of formula (VII)

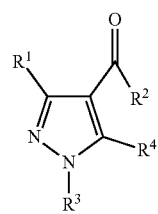

(VII)

wherein
R¹ is selected from the group consisting of $CF_2Cl$, $CF_2H$, $CFCl_2$, $CFClH$, $CF_2Br$, $CCl_3$, $CF_3$, $CBr_3$, and $CI_3$;

R² is $CHal_3$ wherein Hal is a halogen and each Hal is selected independently;

wherein, when R² is $CF_3$, R¹ contains two, one or zero fluorine atoms or, when R² is $CCl_3$, R¹ contains two, one or zero chlorine atoms, R³ is selected from the group consisting of $C_1$-$C_{12}$-alkyl, $C_2$-$C_6$ alkenyl, cycloalkyl, aryl, heteroaryl, and aralkyl;

R⁴ is selected from the group consisting of H, X', COOR', OR', SR', C(O)NR'₂, wherein R' are selected independently in C(O)NR'₂ where R' is hydrogen or a $C_1$-$C_{12}$-alkyl group, CN, $C_1$-$C_{12}$-alkyl, $C_2$-$C_6$ alkenyl, aryl, cycloalkyl, aralkyl, heteroaryl, each of which is optionally substituted, and X' is F, Cl, Br, or I; with a base.

8. The process according to claim 4, wherein the compound of formula (II) is present in the form of a carboxylate (XIII), and wherein the reaction mixture comprising the compound of formula (XIII) is subjected to acidification to obtain the free carboxylic acid (II) with $R^{10}$=H.

9. The process according to claim 4, wherein R¹ is selected from the group consisting of $CF_2Cl$, $CF_2H$, $CFCl_2$, $CFClH$, $CF_3$ and $CF_2Br$.

10. The process according to claim 9, wherein R² is selected from the group consisting of $CCl_3$, $CF_3$ and $CBr_3$.

11. The process according to claim 4, the process comprising the step of reacting a compound of formula (IVa) with a compound of formula (Va) or (Vb) to obtain compound (I)

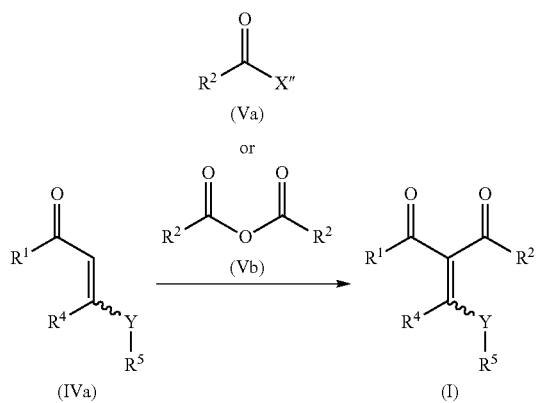

or comprising the step of reacting a compound of formula (IVb) with a compound of formula (Vc) or (Vd) to obtain compound (I)

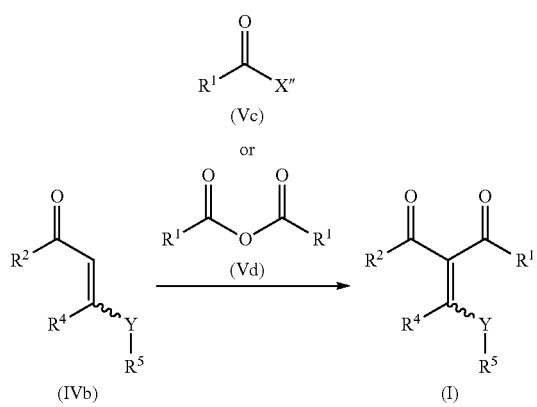

wherein
R¹ is selected from the group consisting of $CF_2Cl$, $CF_2H$, $CFCl_2$, $CFClH$, $CF_2Br$, $CCl_3$, $CF_3$, $CBr_3$, and $CI_3$;

R² is $CHal_3$ wherein Hal is a halogen and each Hal is selected independently;

wherein, when $R^2$ is $CF_3$, $R^1$ contains two, one or zero fluorine atoms or, when $R^2$ is $CCl_3$, $R^1$ contains two, one or zero chlorine atoms, Y is selected from the group consisting of S, O and $NR^6$, $R^4$ is selected from the group consisting of H, X', COOR', OR', SR', C(O)NR'$_2$, wherein R' are selected independently in C(O)NR'2 where R' is hydrogen or a $C_1$-$C_{12}$-alkyl group, CN, $C_1$-$C_{12}$-alkyl, $C_2$-$C_6$ alkenyl, aryl, cycloalkyl, aralkyl, heteroaryl, each of which is optionally substituted, and X' is F, $C_1$, Br, or I;

$R^5$ and $R^6$ independently are selected from the group consisting of $C_1$-$C_{12}$-alkyl, $C_2$-$C_6$ alkenyl or $C_3$-$C_{10}$-cycloalkyl group, each of which is optionally substituted or, when Y=$NR^6$, $R^5$ together with $R^6$ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members;

X" is selected from the group consisting of F, Cl, Br and I.

12. The process according to claim 11, wherein the step of reacting a compound of formula (IVa) with a compound of formula (Va) or (Vb) or the step of reacting a compound of formula (IVb) with a compound of formula (Vc) or (Vd) is performed in the presence of at least one base.

13. The process according to claim 11, further comprising the step of reacting a compound of formula (VIa) or (VIb) to obtain a compound of formula (IVa) or (IVb), wherein in (IVa) and (IVb), Y=$NR^6$, wherein LG is a suitable leaving group, according to the following reaction scheme

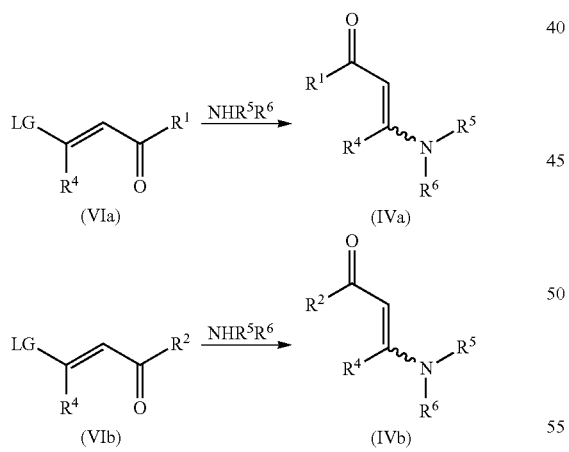

wherein
$R^1$ is selected from the group consisting of $CF_2Cl$, $CF_2H$, $CFCl_2$, $CFClH$, $CF_2Br$, $CCl_3$, $CF_3$, $CBr_3$, and $C_{13}$;

$R^2$ is $CHal_3$ wherein Hal is a halogen and each Hal is selected independently;

wherein, when $R^2$ is $CF_3$, $R^1$ contains two, one or zero fluorine atoms or, when $R^2$ is $CCl_3$, $R^1$ contains two, one or zero chlorine atoms, $R^4$ is selected from the group consisting of H, X', COOR', OR', SR', C(O)NR'$_2$, wherein R' are selected independently in C(O)NR'$_2$ where R' is hydrogen or a $C_1$-$C_{12}$-alkyl group, CN, $C_1$-$C_{12}$-alkyl, $C_2$-$C_6$ alkenyl, aryl, cycloalkyl, aralkyl, heteroaryl, each of which is optionally substituted, and X is F, Cl, Br, or I;

$R^5$ and $R^6$ independently are selected from the group consisting of $C_1$-$C_{12}$-alkyl, $C_2$-$C_6$ alkenyl or $C_3$-$C_{10}$-cycloalkyl group, each of which is optionally substituted or, $R^5$ together with $R^6$ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members.

14. A process for the manufacture of an agrochemical or pharmaceutical compound, of Formula IX,

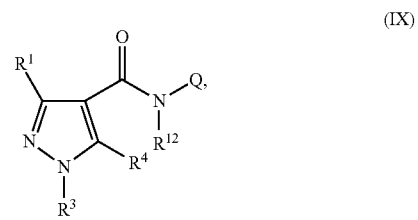

wherein: $R^1$ is selected from the group consisting of $CF_2Cl$, $CF_2H$, $CFCl_2$, $CFClH$, $CF_2Br$, $CCl_3$, $CF_3$, $CBr_3$, and $Cl_3$; $R^3$ is selected from the group consisting of $C_1$-$C_{12}$-alkyl, $C_2$-$C_6$ alkenyl, cycloalkyl, aryl, heteroaryl, and aralkyl; $R^4$ is selected from the group consisting of H, X', COOR', OR', SR', C(O)NR'$_2$, wherein R' are selected independently in C(O)NR'$_2$ where R' is hydrogen or a $C_1$-$C_{12}$-alkyl group, $C_1$-$C_{12}$-alkyl, $C_2$-$C_6$ alkenyl, aryl, cycloalkyl, aralkyl, heteroaryl, each of which is optionally substituted; X' is F, Cl, Br, or I; and $R^{12}$ is selected from the group consisting of H, $C_1$-$C_{12}$-alkyl, $C_2$-$C_6$ alkenyl or $C_3$-$C_8$-cycloalkyl group; wherein a compound of Formula (VII),

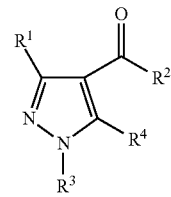

wherein $R^2$ is $CHal_3$ wherein Hal is a halogen and each Hal is selected independently; wherein, when $R^2$ is $CF_3$, $R^1$ contains two, one or zero fluorine atoms or, when $R^2$ is $CCl_3$, $R^1$ contains two, one or zero chlorine atoms; is reacted with at least one amine of formula (VI), $NR^{12}HQ$, wherein $R^{12}$ is selected from the group consisting of H, $C_1$-$C_{12}$ alkyl, $C_2$-$C_6$ alkenyl or $C_3$-$C_8$-cycloalkyl group, and wherein Q is an optionally substituted aryl or heteroaryl group.

15. The process according to claim 14, wherein $R^1$ is selected from the group consisting of $CF_2H$, $CF_3$ and $CCl_2H$.

16. A process for the manufacture of a compound of formula (II), (VII) or (XIII),

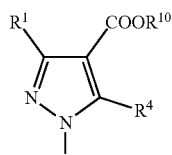

(II)

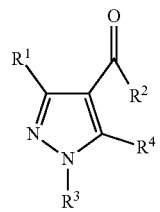

(VII)

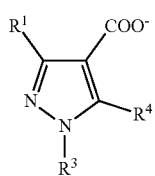

(XIII)

wherein
R$^1$ is selected from the group consisting of CF$_2$Cl, CF$_2$H, CFCl$_2$, CFClH, CF$_2$Br, CCl$_3$, CF$_3$, CBr$_3$, and CI$_3$;
R$^2$ is CHal$_3$ wherein Hal is a halogen and each Hal is selected independently;
wherein, when R$^2$ is CF$_3$, R$^1$ contains two, one or zero fluorine atoms or,
when R$^2$ is CCl$_3$, R$^1$ contains two, one or zero chlorine atoms,
R$^3$ is selected from the group consisting of C$_1$-C$_{12}$-alkyl, C$_2$-C$_6$ alkenyl, cycloalkyl, aryl, heteroaryl, and aralkyl;
R$^4$ is selected from the group consisting of H, X', COOR', OR', SR', C(O)NR'$_2$, wherein R' are selected independently in C(O)NR'$_2$ where R' is hydrogen or a C$_1$-C$_{12}$-alkyl group, CN, C$_1$-C$_{12}$-alkyl, C$_2$-C$_6$ alkenyl, aryl, cycloalkyl, aralkyl, heteroaryl, each of which is optionally substituted, and X' is F, C$_1$, Br, or I;
R$^{10}$ is selected from the group consisting of H, C$_1$-C$_{12}$-alkyl, C$_2$-C$_6$ alkenyl or C$_3$-C$_8$-cycloalkyl group, each of which is optionally substituted;
the process comprising the step of reacting a compound of formula (XII) according to claim 1 with a compound of formula (III), (VIII) or (V),

H$_2$N—NHR$^3$ (III)

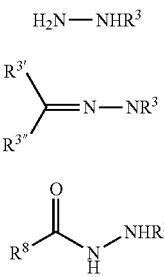

(VIII)

(V)

wherein R$^3$ in (III) and (V) is, or R$^3$, R$^{3'}$ and R$^{3''}$ independently from each other in (VIII) are, selected from the group consisting of C$_1$-C$_{12}$-alkyl, C$_2$-C$_6$ alkenyl, cycloalkyl, aryl, heteroaryl, aralkyl, and for R$^{3'}$ and R$^{3''}$ H, each of which is optionally substituted, R$^8$ is selected from the group consisting of R$^9$=C$_1$-C$_{12}$-alkyl, OR$^9$ and NR$^{11}$R$^{11'}$, wherein R$^{11}$ and R$^{11'}$ independently are selected from the group consisting of C$_1$-C$_{12}$-alkyl and H;

which is optionally performed in the presence of a base, and which optionally comprises a step of acidification of a reaction mixture comprising a compound of formula (XIII).

17. A compound of formula (XIV),

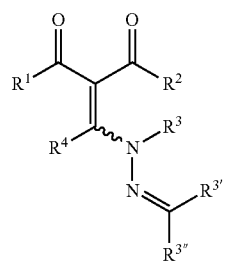

(XIV)

wherein
R$^1$ is selected from the group consisting of CF$_2$Cl, CF$_2$H, CFCl$_2$, CFClH, CF$_2$Br, CCl$_3$, CF$_3$, CBr$_3$, and CI$_3$;
R$^2$ is CHal$_3$ wherein Hal is a halogen and each Hal is selected independently;
wherein, when R$^2$ is CF$_3$, R$^1$ contains two, one or zero fluorine atoms or,
when R$^2$ is CCl$_3$, R$^1$ contains two, one or zero chlorine atoms,
R$^3$, R$^{3'}$ and R$^{3''}$ independently from each other are selected from the group consisting of C$_1$-C$_{12}$-alkyl, C$_2$-C$_6$ alkenyl, cycloalkyl, aryl, heteroaryl, aralkyl, and for R$^{3'}$ and R$^{3''}$ H, each of which is optionally substituted;
R$^4$ is selected from the group consisting of H, X', COOR', OR', SR', C(O)NR'$_2$, wherein R' are selected independently in C(O)NR'$_2$ where R' is hydrogen or a C$_1$-C$_{12}$-alkyl group, CN, C$_1$-C$_{12}$-alkyl, C$_2$-C$_6$ alkenyl, aryl, cycloalkyl, aralkyl, heteroaryl, each of which is optionally substituted, and X' is F, Cl, Br, or I.

18. A process for the manufacture of a compound of formula (II), (VII) or (XIII)

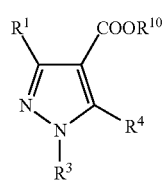

(II)

-continued

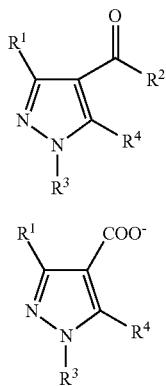

(VII)

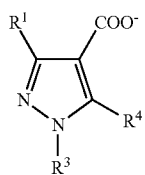

(XIII)

wherein
R¹ is selected from the group consisting of $CF_2Cl$, $CF_2H$, $CFCl_2$, $CFClH$, $CF_2Br$, $CCl_3$, $CF_3$, $CBr_3$, and $CI_3$;

R² is $CHal_3$ wherein Hal is a halogen and each Hal is selected independently;
wherein, when R² is $CF_3$, R¹ contains two, one or zero fluorine atoms or,
when R² is $CCl_3$, R¹ contains two, one or zero chlorine atoms,
R³ is selected from the group consisting of $C_1$-$C_{12}$-alkyl, $C_2$-$C_6$ alkenyl, cycloalkyl, aryl, heteroaryl, and aralkyl;
R⁴ is selected from the group consisting of H, X', COOR', OR', SR', C(O)NR'₂, wherein R' are selected independently in C(O)NR'₂ where R' is hydrogen or a $C_1$-$C_{12}$-alkyl group, CN, $C_1$-$C_{12}$-alkyl, $C_2$-$C_6$ alkenyl, aryl, cycloalkyl, aralkyl, heteroaryl, each of which is optionally substituted, and X is F, Cl, Br, or I;
R¹⁰ is selected from the group consisting of H, $C_1$-$C_{12}$-alkyl, $C_2$-$C_6$ alkenyl or $C_3$-$C_8$-cycloalkyl group, each of which is optionally substituted;
the process comprising reacting compound of formula (XIV) according to claim 17 with an acid.

* * * * *